(12) United States Patent
Sorensen

(10) Patent No.: US 10,767,127 B2
(45) Date of Patent: Sep. 8, 2020

(54) CHEMICALS AND FUEL BLENDSTOCKS BY A CATALYTIC FAST PYROLYSIS PROCESS

(71) Applicant: ANELLOTECH, INC., Pearl River, NY (US)

(72) Inventor: Charles Sorensen, Haverstraw, NY (US)

(73) Assignee: ANELLOTECH, INC., Pearl River, NY (US)

( * ) Notice: Subject to any disclaimer, the term of this patent is extended or adjusted under 35 U.S.C. 154(b) by 33 days.

(21) Appl. No.: 16/071,240

(22) PCT Filed: Jan. 23, 2017

(86) PCT No.: PCT/US2017/014584
§ 371 (c)(1),
(2) Date: Jul. 19, 2018

(87) PCT Pub. No.: WO2017/136178
PCT Pub. Date: Aug. 10, 2017

(65) Prior Publication Data
US 2019/0382665 A1    Dec. 19, 2019

Related U.S. Application Data

(60) Provisional application No. 62/291,615, filed on Feb. 5, 2016.

(51) Int. Cl.
*C10L 1/16*    (2006.01)
*C10G 1/00*    (2006.01)
(Continued)

(52) U.S. Cl.
CPC .............. *C10L 1/1608* (2013.01); *C07C 5/10* (2013.01); *C10B 53/02* (2013.01); *C10B 57/06* (2013.01); *C10G 1/002* (2013.01); *C10G 1/083* (2013.01); *C10G 1/086* (2013.01); *C10G 45/54* (2013.01); *C10G 45/56* (2013.01); *C10L 1/06* (2013.01); *C10L 1/1266* (2013.01);
(Continued)

(58) Field of Classification Search
CPC . C10G 1/00; C10G 1/08; C10G 45/56; C10G 45/54; C07C 5/10
See application file for complete search history.

(56) References Cited

U.S. PATENT DOCUMENTS 3,597,489 A    8/1971  Vu et al.
4,330,302 A    5/1982  Taylor
(Continued)

OTHER PUBLICATIONS

S. Jones et al. "Process Design and Economics for the Conversion of Lignocellulosic Biomass to Hydrocarbon Fuels: Fast Pyrolysis and Hydrotreating Bio-oil Pathway," PNNL-23053, Nov. 2013, available electronically at http://www.osti.gov/bridge.
(Continued)

*Primary Examiner* — Youngsul Jeong
(74) *Attorney, Agent, or Firm* — Roberts Calderon Safran & Cole P.C.

(57) ABSTRACT

The present invention provides a catalytic fast pyrolysis process for the production of fuel blendstocks and chemicals. In addition, the invention provides compositions of renewable blendstocks, compositions of renewable fuel blends, and compositions of 100 percent renewable fuels compatible with gasoline specifications and regulations.

17 Claims, 7 Drawing Sheets

(51) Int. Cl.
    *C10G 45/54*         (2006.01)
    *C10G 45/56*         (2006.01)
    *C07C 5/10*           (2006.01)
    *C10L 1/06*           (2006.01)
    *C10L 1/12*           (2006.01)
    *C10B 53/02*         (2006.01)
    *C10B 57/06*         (2006.01)
    *C10G 1/08*          (2006.01)

(52) U.S. Cl.
    CPC ........... *C10L 1/1275* (2013.01); *C10L 1/1691* (2013.01); *C07C 2521/12* (2013.01); *C07C 2529/40* (2013.01); *C07C 2601/14* (2017.05); *C10G 2300/1011* (2013.01); *C10G 2300/202* (2013.01); *C10G 2300/305* (2013.01); *C10G 2400/02* (2013.01); *C10G 2400/30* (2013.01); *C10L 2200/0469* (2013.01); *C10L 2270/023* (2013.01)

(56) References Cited

U.S. PATENT DOCUMENTS

| | | | |
|---|---|---|---|
| 4,549,031 A * | 10/1985 | Chen | ......................... C07C 1/20 585/408 |
| 8,277,643 B2 | 10/2012 | Huber et al. | |
| 8,277,684 B2 | 10/2012 | Klasen-Memmer et al. | |
| 8,864,984 B2 | 10/2014 | Huber et al. | |
| 9,062,264 B2 | 6/2015 | Ramirez Corredores et al. | |
| 2003/0183554 A1 | 10/2003 | Bazzani et al. | |
| 2009/0193710 A1 | 8/2009 | Xiong et al. | |
| 2012/0151824 A1 | 6/2012 | Kalnes | |
| 2012/0203042 A1 | 8/2012 | Huber et al. | |
| 2013/0060070 A1 | 3/2013 | Huber et al. | |
| 2013/0219777 A1 | 8/2013 | Xiong et al. | |
| 2013/0324772 A1 | 12/2013 | Huber et al. | |
| 2014/0027265 A1 | 1/2014 | Mazanec et al. | |
| 2014/0107306 A1 | 4/2014 | Mazanec et al. | |
| 2014/0303414 A1 | 10/2014 | Mazanec et al. | |
| 2016/0002544 A1 * | 1/2016 | Sorensen, Jr. | ......... C10G 45/32 585/24 |

OTHER PUBLICATIONS

International Search Report and Written Opinion issued in the corresponding application No. PCT/US2017/014584 dated May 2, 2017.

Bridgwater AV et al: "Fast pyrolysis processes for biomass", Renewable and Sustainable Energy Reviews, Elseviers Science, New York, NY, US, vol. 4, No. 1, Mar. 1, 2000 (Mar. 1, 2000), pp. 1-73.

Villaluenga et al., A review on the separation of benzene/cyclohexane mixtures by pervaporation processes, Journal of Membrane Science 169 (2000) 159-174.

* cited by examiner

CHEMICALS AND FUEL BLENDSTOCKS BY A CATALYTIC FAST PYROLYSIS PROCESS

CROSS-REFERENCE TO RELATED APPLICATIONS

The present application is a U.S. National Phase of PCT/US2017/014584 filed on Jan. 23, 2017, claiming priority to U.S. Provisional Patent Application No. 62/291,615 filed Feb. 5, 2016. The disclosure of the PCT Application is hereby incorporated by reference into the present application.

FIELD OF THE INVENTION

The present invention relates to an improved catalytic fast pyrolysis process. In particular, it relates to an improved process to produce fuel blendstocks and chemicals from renewable feedstocks via catalytic fast pyrolysis, and to the chemicals, fuel blendstocks, and fuel compositions produced thereby.

BACKGROUND OF THE INVENTION

A modern oil refinery converts crude oil through numerous unit operations and conversion reactions into several individual streams, called including diesel, jet fuel, and gasoline blendstocks that are stored in separate tanks so they can be blended together in calculated proportions to obtain various grades of "finished" gasoline that consumers purchase at the service station pump. The gasoline product is a complex blend of hydrocarbons that is subject to a variety of technical and regulatory limitations on the concentrations of certain individual chemical compounds, chemical elements, and classes of chemical components. Examples include limits on the amount of benzene allowed in finished gasoline (currently 0.62% by volume), limits on the amount of organo-sulfur compounds which are limited indirectly by a specification of the total amount of the element sulfur (currently 30 ppm), and limits on the total amounts of aromatics and olefins, either directly for reformulated gasoline or indirectly through limits calculated by the so-called "complex model" for air toxics as administered by the US EPA. There are also physical property limits to gasoline such as its Reid Vapor Pressure (RVP), and distillation mid and end points.

In the United States there are additional laws that require gasoline, jet, and diesel fuels to contain renewable-sourced blendstocks between specific minimum and maximum levels. Today those limits are set by Congress via the Renewable Fuels Standards ("RFS"). The RFS mandates that 21 billion gallons of advanced biofuels will need to be produced by 2022. A part of these advanced biofuels will be fungible transportation fuels such as gasoline, jet fuel, and diesel derived from biomass. Efforts continue on producing such fuels from biomass to meet the mandate and it is perceived that there will be a strong demand for gasoline, jet, and diesel fuels produced economically from biomass. The chief renewable-sourced gasoline blendstock used in the U.S. to meet the gasoline blending requirement is ethanol, produced largely from corn or sugar fermentation. A minor, but growing contribution to the nation's renewable gasoline pool is so-called "second generation" cellulosic ethanol made from non-food biomass such as corn stover.

There are several issues that make ethanol a less-desirable renewable gasoline blendstock. One of these is that most ethanol is produced from corn, which otherwise could be used for human or animal food. Furthermore, the land used to grow corn for ethanol production could be re-purposed to grow other kinds of food crops if other sources of renewable fuels besides ethanol could be produced. This is a societal issue that is a disadvantage for ethanol production; there are also many technical disadvantages of ethanol.

The technical disadvantages of ethanol as a fuel blendstock include the fact that ethanol is hygroscopic and therefore cannot be transported in pipelines that are used to ship conventional gasoline or other pure hydrocarbon products, otherwise water drop-out and pipeline corrosion issues may occur. This has resulted in the establishment of a separate ethanol supply chain and infrastructure, and the need for "splash blending" to make the final gasoline composition. Splash blending occurs when ethanol is added to gasoline at the gasoline distribution and tanker truck depot which makes it more difficult for refineries to optimize their intermediate "base" gasoline formulations (e.g. Reformulated Gasoline Blendstock for Oxygen Blending or "RBOB", and Conventional Blendstock for Oxygenate Blending or "CBOB") that become "finished" gasoline after ethanol addition. This can result in sub-optimal compositions that lead to "octane giveaway", meaning that consumers might receive gasoline at a higher octane rating than what is stated on the service station pump label.

Further, ethanol has been shown to have a detrimental effect on certain elastomer sealing materials used in some gasoline engines and fuel systems. This problem is worse for older engines and for non-road engines such as those used for recreational vehicles such as boats and four wheelers.

Another disadvantage of ethanol as a fuel blendstock is that ethanol has lower energy density than typical gasoline components because it is a polar molecule that contains the element oxygen. Compared to gasoline, ethanol has approximately 32% lower energy density per liquid volume of product. The energy density of gasoline ranges from 112,000 to 116,000 BTU/gal (44-46 MJ/kg), whereas ethanol is 76,000 BTU/gal (30 MJ/kg).

An important technical disadvantage of ethanol is its very high blending Reid Vapor Pressure (RVP). RVP is the absolute vapor pressure exerted by a material at 100° F. (37.8° C.). Blending RVP represents the material's contribution to the RVP of a mixture such that the RVP for the mixture equals the summation of each component's blend RVP multiplied by some function of that component's volume fraction. Although pure ethanol has a relatively low RVP, the vapor pressures of ethanol-gasoline blends are higher than expected from simple mixing due to non-ideal vapor-liquid solution thermodynamics that occur because of the presence of the alcohol functional group. Ethanol has a blending RVP of more than 20 psi when blended at 10 volume percent in gasoline. It is important to note that there is no single best volatility for gasoline. Volatility must be adjusted for the altitude and seasonal temperature of the location where the gasoline will be used. To meet strict RVP limits on finished gasoline, especially for summertime blends, refiners reduce the vapor pressures of the base gasoline blends to low levels, prior to ethanol splash blending. The lower vapor pressure limit forces refiners to "back out" relatively lower value materials such as butanes, pentanes, and other hydrocarbon components from gasoline, which creates additional costs.

Because of the fundamental limitation of ethanol-containing gasoline blend vapor pressure, the U.S. EPA has relaxed the finished gasoline RVP specification for blends having 10% (volume) ethanol. These blends are allowed to have an RVP limit that is 1 psi higher than gasoline that contains no alcohol. The higher vapor pressure of the ethanol containing gasoline results in more evaporative emissions and resultant air pollution problems.

In the manufacture of ethanol by fermentation, various sources of sulfur are present including a relatively high level sulfur in the corn feedstock (e.g. up to 1200 ppm in corn versus 500 ppm in pine and hardwoods), sulfur in the fermentation yeast, and the use of several sulfur-containing acids to adjust pH, clean equipment, and remove aldehydes from $CO_2$ (e.g. sulfuric acid, sulfamic acid, and sodium bisulfite respectively). These contribute a relatively high level of sulfur in ethanol blendstocks. Currently ASTM4806-15 is the standard regulating the specifications for fuel ethanol and it allows total sulfur content up to 30 ppm, and sulfate is limited to 4 ppm maximum. Soon the limit on sulfur permitted in gasoline sold in the United States will be reduced to 10 ppm maximum. The reduced sulfur limit will require refiners to reduce the sulfur content of their base gasolines further to accommodate the high level of sulfur in the ethanol splash blend.

Biodiesel is a fuel having a fatty acid methyl ester (Fatty Acid Methyl Ester: FAME) component obtained by methyl esterification of fats and oils derived from living things by way of various methods. However, if the additive amount of biodiesel exceeds a certain value, the amount of heat generation by the diesel engine will decrease, and it will not be possible to heat the diesel particulate filter (DPF) to high temperature and it will clog. In addition, the generation of injector deposits and combustion deposits, causes deterioration of some fuel hoses resulting in unsafe vehicle operation. High concentrations of biodiesel can cause sludge formation and oxidative degradation, which may induce clogging of the injectors, fuel filter, piping and the like, in addition to adversely affecting vehicle performance. As a result, use of biodiesel requires special allowances and frequent component replacement, and its use is limited to 5% by volume. Therefore, a renewable diesel fuel blendstock has been sought that can be blended in high concentrations and used without special considerations.

For civilian or commercial aircraft, there are two main grades of jet fuel: Jet A-1 and Jet A. Jet fuels of both grades are kerosene-type fuel and the difference between them is that Jet A-1 fulfills the freezing point requirement of maximum −47° C., whereas Jet A fulfills the freezing point requirement of maximum −40° C. There is another grade of jet fuel: Jet B for usage in a very cold climate, a wide-cut fuel covering fractions from naphtha and kerosene, which fulfills the freezing point requirement of maximum −50° C. Jet fuels generally comprise at least 50% by weight hydrocarbon compounds with from 5 to 16 carbon atoms.

Biomass pyrolysis has been developing as an alternative to ethanol for providing renewable fuels and fuel blendstocks. The product of biomass pyrolysis is a complex and unstable bio oil whose composition varies widely depending on feedstock and pyrolysis conditions, and that comprises hundreds of compounds including a plethora of oxygenates. Generally bio oil contains 20-40% by weight oxygen and a small percentage of sulfur-containing materials. Hydrotreatment of the bio oil, including hydrodeoxygenation (HDO), hydrodesulfurization (HDS), and olefin hydrogenation, is required to make the oil suitable as a blendstock or stand-alone fuel. While hydrotreating is well developed for petroleum feedstocks that contain almost no oxygen, the challenges of hydrotreating bio oil are more substantial. To date the preferred processes for hydrotreating bio oil are multi-stage systems that require high pressure of hydrogen, precious metal catalysts, and multiple unit operations (see for example, "Process Design and Economics for the Conversion of Lignocellulosic Biomass to Hydrocarbon Fuels: Fast Pyrolysis and Hydrotreating Bio-oil Pathway," S. Jones et al, PNNL-23053, November 2013, available electronically at http://www.osti.gov/bridge).

Catalytic fast pyrolysis of biomass has been developed as an improved thermal process for upgrading biomass to chemicals and fuels. The process involves the conversion of biomass in a fluid bed reactor in the presence of a catalyst. The catalyst is usually an acidic, microporous crystalline material, usually a zeolite. The zeolite is active for the upgrading of the primary pyrolysis products of biomass decomposition, and converts them to aromatics, olefins, CO, CO2, char, coke, water, and other useful materials. The aromatics include benzene, toluene, xylenes, (collectively BTX), and naphthalene, among other aromatics. The olefins include ethylene, propylene, and lesser amounts of higher molecular weight olefins. BTX aromatics are desirable products due to their high value and ease of transport. Toluene and xylenes are particularly desirable as gasoline components due to their high octane rating and energy density. Heavier aromatics are suitable precursors to jet and diesel fuels. When produced under proper conditions, the products of catalytic fast pyrolysis are very low in oxygen content.

U.S. Pat. No. 9,062,264 discloses a process and system for producing a renewable gasoline by separating a bio-gasoline fraction from bio oil, and directly blending it with a petroleum-derived gasoline, without any prior hydrotreatment. The disclosure also describes bio-gasoline compositions derived from lignocellulosic biomass catalytically pyrolyzed in a riser reactor in which the bio-gasoline contains hydrocarbons and oxygenates wherein phenolic compounds comprise at least 10% by weight, or carbon- and oxygen-containing compounds comprise at least 15% by weight of the bio-gasoline.

U.S. Pat. Nos. 8,277,684 and 8,864,984 disclose that products from a catalytic fast pyrolysis process using zeolites such as HZSM-5 as catalyst contain aromatics, that the products have high octane and can be used directly as fuels or as fuel additives, and a method for producing a biofuel or fuel additive composition with an octane number of at least 90 from a solid hydrocarbonaceous biomass material. However, without further processing only very minute quantities of the raw product mixture can be blended into gasoline to produce a gasoline blend that meets regulatory specifications. The disclosures do not address the conditions or processes required to produce a gasoline blendstock, the amount of fuel additive that could be used in a gasoline blending base stock or in a finished gasoline composition, or the properties of such a blended fuel. The disclosures do not suggest the removal of heteroatom contaminants, such as sulfur, nitrogen, and oxygenates, how to achieve a product that meets the allowable limits of dienes, vinyl-aromatics (e.g. styrene), and olefins in the product, nor how to achieve various gasoline blend specifications. The disclosures do not suggest concepts or process configurations to produce C5/C6 naphtha, cyclohexane, linear alkyl benzenes, or naphthenes.

In U. S. Patent Publication No. 2014/0107306 A1, a method and apparatus are described for pyrolysis of biomass and conversion of at least one pyrolysis product to another chemical compound. The latter method comprises feeding a hydrocarbonaceous material to a reactor, pyrolyzing within the reactor at least a portion of the hydrocarbonaceous material under reaction conditions sufficient to produce one or more pyrolysis products, catalytically reacting at least a portion of the pyrolysis products, separating at least a portion of the hydrocarbon products, and reacting a portion of the hydrocarbon products to produce a chemical intermediate.

In U.S. Pat. Nos. 8,277,643; 8,864,984; U.S. Patent Publication 2012/0203042 A1; U. S. Patent Publication 2013/0060070 A1, U. S. Patent Publication 2014/0027265 A1; and US Patent Publication 2014/0303414 A1, each incorporated herein by reference in its entirety, apparatus and process conditions suitable for catalytic fast pyrolysis are described.

In light of current commercial practices and the disclosures of art, a simple economical process for producing renewable gasoline blending stocks, diesel fuels, or jet fuels that meet technical and regulatory limitations by use of catalytic pyrolysis of biomass is needed. The present invention provides such a process and the resulting blend compositions and chemicals.

SUMMARY OF THE INVENTION

Various aspects of the present invention include increased yield of fuel blendstocks and chemicals from renewable feedstocks via catalytic fast pyrolysis (CFP). The present invention provides for this in an economical improved process. An embodiment of the present process comprises the steps of: a) feeding biomass, catalyst composition, such as one comprising a crystalline molecular sieve characterized by a silica/alumina mole ratio (SAR) greater than 12 and a Constraint Index (CI) from 1 to 12, and transport fluid to a CFP process fluidized bed reactor maintained at reaction conditions to manufacture a raw fluid product stream, b) feeding the raw fluid product stream of step a) to a solids separation and stripping system to produce separated solids and a fluid product stream, c) feeding the fluid product stream of step b) to a quench vapor/liquid separation system utilizing water or hydrocarbon quench to produce a liquid phase stream comprising water, char, coke, ash, catalyst fines, oxygenates, and $C_9^+$ aromatics, and a vapor phase stream comprising carbon monoxide, carbon dioxide, hydrogen, olefins, and aromatics, said aromatics of the vapor phase stream selected from the group consisting of benzene, toluene, xylenes, phenols, naphthols, benzofuran, ethylbenzene, styrene, naphthalene, methylnaphthalene and combinations thereof, d) feeding the vapor phase stream of step c) to a condensation system to produce an organic phase stream, e) feeding the organic phase stream of step d) to a separation system to produce a high boiling fraction, such as one boiling at 185° C. and higher, and a low boiling fraction, such as one boiling below 185° C., f) hydrotreating at least a portion of the low boiling fraction of step e) at hydrotreating conditions to produce a hydrotreated fraction, and g) recovering fuel, such as gasoline, blendstock comprising less than 0.4 weight % olefins, less than 10 ppm by weight sulfur, less than 10 ppm by weight nitrogen, and less than 1 weight % oxygen, from the hydrotreated fraction of step f) in a product recovery system. Boiling ranges presented in this invention refer to the boiling ranges under modest pressure operation, typically 0.1 MPa, or from 0.05 to 1 MPa.

In another embodiment of the present invention, the blendstock recovered in step g) further comprises at least 25, e.g. 25 to 60, volume % toluene, at least 15, e.g. 15 to 40, volume % benzene, at least 5, e.g. 5 to 20, volume % xylenes, less than 15, e.g. 0.01 to <15, volume % C9+ aromatics, and less than 10, e.g. 0.5 to <10, volume % paraffins, said blendstock having a calculated octane rating ((R+M)/2) of at least 100, and a calculated RVP of less than 5 psia.

In another embodiment of the present invention, the blendstock recovered in step g) further comprises at least 75, e.g. 75 to 99.9, volume % benzene, less than 20, e.g. 1 to <20, volume % total pentanes and hexanes, and less than 20, e.g. 1 to <20, volume % total toluene, xylenes, ethylbenzene and trimethylbenzenes, said blendstock having a calculated octane rating ((R+M)/2) of at least 99, and a calculated RVP of less than 7 psia.

In another embodiment of the present invention, the blendstock recovered in step g) further comprises at least 50, e.g. 50 to 99, volume % toluene, less than 15, e.g. 0.1 to <15, volume % benzene, at least 10, e.g. 10 to 40, volume % xylenes, less than 15, e.g. 1 to <15, volume % C9+ aromatics, and less than 2, e.g. 0.01 to <2, volume % paraffins, said blendstock having a calculated octane rating ((R+M)/2) of at least 100, and a calculated RVP of less than 3 psia.

In another embodiment of the present invention, the blendstock recovered in step g) further comprises less than 1, e.g. 1 ppm to <1, volume % benzene, less than 10, e.g. 1 to <10, volume % total pentanes and hexanes, less than 1, e.g. 1 ppm to <1, weight % total of the sum of toluene, xylenes, trimethylbenzenes and naphthalene, and at least 80, e.g. 80 to 99, volume % cyclohexane, said blendstock having a calculated octane rating ((R+M)/2) of at least 75, and a calculated RVP of less than 7 psia.

In another embodiment of the present invention the blendstock recovered in step g) further comprises less than 1 volume % benzene, less than 10 volume % total pentanes and hexanes, less than 1 weight % toluene, less than 1 weight % xylenes, less than 1 weight % trimethylbenzenes and naphthalene, and at least 80 volume % cyclohexanes comprising cyclohexane, and methyl-, dimethyl-, ethyl-, methyl-ethyl- or propyl-alkylated cyclohexanes, said blendstock having a calculated octane rating ((R+M)/2) of at least 70, and a calculated RVP of less than 7 psia.

In another embodiment of the present invention the blendstock recovered in step g) further comprises 50 to 99 volume % the sum of cyclohexane, methyl-cyclohexane, dimethyl-cyclohexane, ethyl-cyclohexane, methyl-ethyl-cyclohexane, and propyl-cyclohexanes, less than 15 volume % benzene, from 0.01 to 2 volume % paraffins, less than 0.4 weight % olefins, less than 10 ppm by weight sulfur, less than 10 ppm by weight nitrogen, and less than 1 weight % oxygen, said blendstock having a calculated octane rating ((R+M)/2) of at least 70, and a calculated RVP of less than 7 psia. This cyclohexanes-rich blendstock may be mixed with gasoline, or ethanol, or diesel, or jet fuel to produce renewable fuel mixtures. Another embodiment of the invention comprises a mixture of from 90 to 99.9 volume % gasoline and from 0.1 to 10 volume % of the cyclohexanes-rich blendstock. Another embodiment of the invention comprises a mixture of from 50 to 99 volume % ethanol and from 50 to 1 volume % of the cyclohexanes-rich blendstock. Another embodiment of the invention comprises a mixture of from 50 to 99 volume % diesel fuel and from 50 to 1 volume % of the cyclohexanes-rich blendstock. Another embodiment of the invention comprises a mixture of from 50 to 99 volume % jet fuel and from 50 to 1 volume % of the cyclohexanes-rich blendstock.

In another embodiment of the present invention, the blendstock recovered in step g) further comprises at least 30, e.g. 30 to 60, volume % toluene, less than 10, e.g. 1 to <10, volume % benzene, at least 5, e.g. 5 to 25, volume % xylenes, less than 5, e.g. 0.1 to <5, volume % total pentanes and hexanes, less than 10, e.g. 1 to <10, volume % total trimethylbenzenes and naphthalene, and at least 10, e.g. 10 to 40, volume % cyclohexane, said blendstock having a calculated octane rating ((R+M)/2) of at least 95, and a calculated RVP of less than 5 psia.

In another embodiment of the present process, step e) comprises hydrotreating the organic phase stream of step d) at hydrotreating conditions to produce a hydrotreated stream, and step f) comprises feeding the hydrotreated stream of step e) to a separation system to produce a hydrotreated high boiling fraction, such as one boiling at 185° C. and higher, and a hydrotreated low boiling fraction, such as one boiling below 185° C., and step g) comprises recovering fuel blendstock comprising less than 0.4 weight % olefins, less than 10 ppm by weight sulfur, less than 10 ppm by weight nitrogen, and less than 1 weight % oxygen from the hydrotreated low boiling fraction of step f).

Another embodiment of the present process comprises the steps of: i) feeding biomass, catalyst composition, such as one comprising a crystalline molecular sieve characterized by an SAR greater than 12 and a CI from 1 to 12, and transport fluid to a CFP process fluidized bed reactor maintained at reaction conditions to manufacture a raw fluid product stream, ii) feeding the raw fluid product stream of step i) to a solids separation and stripping system to produce separated solids and a fluid product stream, iii) feeding the fluid product stream of step ii) to a quench vapor/liquid separation system utilizing water or hydrocarbon quench to produce a liquid phase stream comprising water, char, coke, ash, catalyst fines, oxygenates, and C9+ aromatics, and a vapor phase stream comprising carbon monoxide, carbon dioxide, hydrogen, olefins, and aromatics, said aromatics of the vapor phase stream selected from the group consisting of benzene, toluene, xylenes, phenols, naphthols, benzofuran, ethylbenzene, styrene, naphthalene, methylnaphthalene and combinations thereof, iv) feeding the vapor phase stream of step iii) to a condensation system to produce an organic phase stream, v) feeding the organic phase stream of step iv) to a separation system to produce a high boiling fraction, such as one boiling at 185° C. and higher, and a low boiling fraction, such as one boiling below 185° C., vi) feeding the low boiling fraction of step v) to a separation system to produce a fraction boiling above 85° C. and a fraction boiling below 85° C., vii) alkylating at least a portion of the fraction boiling below 85° C. of step vi) by contact with an alkylating agent at alkylating conditions to produce an alkylated fraction, or hydrogenating at least a portion of the fraction boiling below 85° C. of step vi) at hydrogenating conditions to produce a hydrogenated fraction, or both, and viii) recovering chemicals comprising ethylbenzene, cumene, propylbenzenes, linear alkylbenzenes wherein the alkyl chain comprises from 10 to 16 carbon atoms, or a combination thereof, from the alkylated fraction of step vii), or chemicals comprising cyclohexane from the hydrogenated fraction of step vii), or both, in a product recovery system.

Another embodiment of the present invention comprises such process wherein the crystalline molecular sieve of the catalyst of step a) or i) has a structure of ZSM-5, ZSM-11, ZSM-12, ZSM-22, ZSM-23, ZSM-35, ZSM-38, ZSM-48, ZSM-50 or combinations thereof.

In another embodiment of the invention, step vi) comprises feeding the low boiling fraction of step v) to a separation system to produce a fraction boiling above 78° C. and a fraction boiling below 78° C., step vii) comprises alkylating at least a portion of the fraction boiling below 78° C. of step vi) by contact with an alkylating agent at alkylating conditions to produce an alkylated fraction, or hydrogenating and at least a portion of the fraction boiling below 78° C. of step vi) at hydrogenating conditions to produce a hydrogenated fraction, or both, and step viii) comprises recovering chemicals comprising ethylbenzene, cumene, propylbenzenes, linear alkylbenzenes wherein the alkyl chain comprises from 10 to 16 carbon atoms from the alkylated fraction of step vi), or chemicals comprising cyclohexane from the hydrogenated fraction of step vi), or both, in a product recovery system.

Another embodiment comprises a fuel blendstock comprising from 25 to 60 volume % toluene, from 15 to 40 volume % benzene, from 5 to 20 volume % xylenes, from 0.01 to 15 volume % $C_9^+$ aromatics, from 0.5 to 10 volume % paraffins, less than 0.4 weight % olefins, less than 10 ppm by weight sulfur, less than 10 ppm by weight nitrogen, and less than 1 weight % oxygen, said blendstock having a calculated octane rating ((R+M)/2) of at least 100, and a calculated RVP of less than 5 psia.

Another embodiment comprises a fuel blendstock comprising from 75 to 99.9 volume % benzene, from 1 to 20 volume % total pentanes and hexanes, from 1 to 20 volume % total toluene, xylenes, ethylbenzene and trimethylbenzenes, less than 0.4 weight % olefins, less than 10 ppm by weight sulfur, less than 10 ppm by weight nitrogen, and less than 1 weight % oxygen, said blendstock having a calculated octane rating ((R+M)/2) of at least 99, and a calculated RVP of less than 7 psia.

Another embodiment comprises a fuel blendstock comprising from 50 to 99 volume % toluene, 10 to 40 volume % xylenes, from 0.1 to 15 volume % benzene, from 1 to 15 volume % $C_9^+$ aromatics, from 0.01 to 2 volume % paraffins, less than 0.4 weight % olefins, less than 10 ppm by weight sulfur, less than 10 ppm by weight nitrogen, and less than 1 weight % oxygen, said blendstock having a calculated octane rating ((R+M)/2) of at least 100, and a calculated RVP of less than 3 psia.

Another embodiment comprises a fuel blendstock comprising from 1 ppm to 1 weight % benzene, from 1 to 10 volume % total pentanes and hexanes, from 1 ppm to 1% by weight total toluene, xylenes, trimethylbenzenes and naphthalene, from 80 to 99 volume % cyclohexane, less than 0.4 weight % olefins, less than 10 ppm by weight sulfur, less than 10 ppm by weight nitrogen, and less than 1 weight % oxygen, said blendstock or chemical stock having a calculated octane rating ((R+M)/2) of at least 75, and a calculated RVP of less than 7 psia.

Another embodiment comprises a fuel blendstock comprising from 30 to 60 volume % toluene, from 1 to 10 volume % benzene, from 5 to 25 volume % xylenes, from 0.1 to 5 volume % total pentanes and hexanes, from 1 to 10 volume % total trimethylbenzenes and naphthalene, from 10 to 40 volume % cyclohexane, less than 0.4 weight % olefins, less than 10 ppm by weight sulfur, less than 10 ppm by weight nitrogen, and less than 1 weight % oxygen, said blendstock having a calculated octane rating ((R+M)/2) of at least 95, and a calculated RVP of less than 5 psia.

In another embodiment of the present process, step e) comprises feeding the organic phase stream of step d) to a separation system to produce a high boiling fraction, such as one boiling at 185° C. and higher, and a low boiling fraction, such as one boiling below 185° C., step f) comprises hydrogenating at least a portion of the fraction boiling above 185° C. of step e) at hydrogenating conditions to produce a hydrogenated fraction, and step g) comprises recovering fuel blendstock components from the hydrogenated fraction of step f). The fuel blendstock prepared in this embodiment may comprise decalin, substituted decalins, e.g. methyl decalin, tetralin, substituted tetralins, e.g. methyl tetralin, and other bicyclic paraffin or aromatic materials. The fuel blendstock prepared in this embodiment may comprise hydrocarbons with from 5 to 16 carbon atoms, or hydrocarbons with at least 9 carbon atoms, or both.

In another embodiment of the invention the hydrogen gas that is utilized for the hydrotreatment or hydrogenation in step f), or step e), or step g), or in any other step, or in multiple steps, is separated from the product gas stream or generated from the product gas stream in a water gas shift reaction, partial oxidation, or gasification of a heavier product fraction, or both separated and generated within the process.

DETAILED DESCRIPTION OF THE INVENTION

Figure 1:
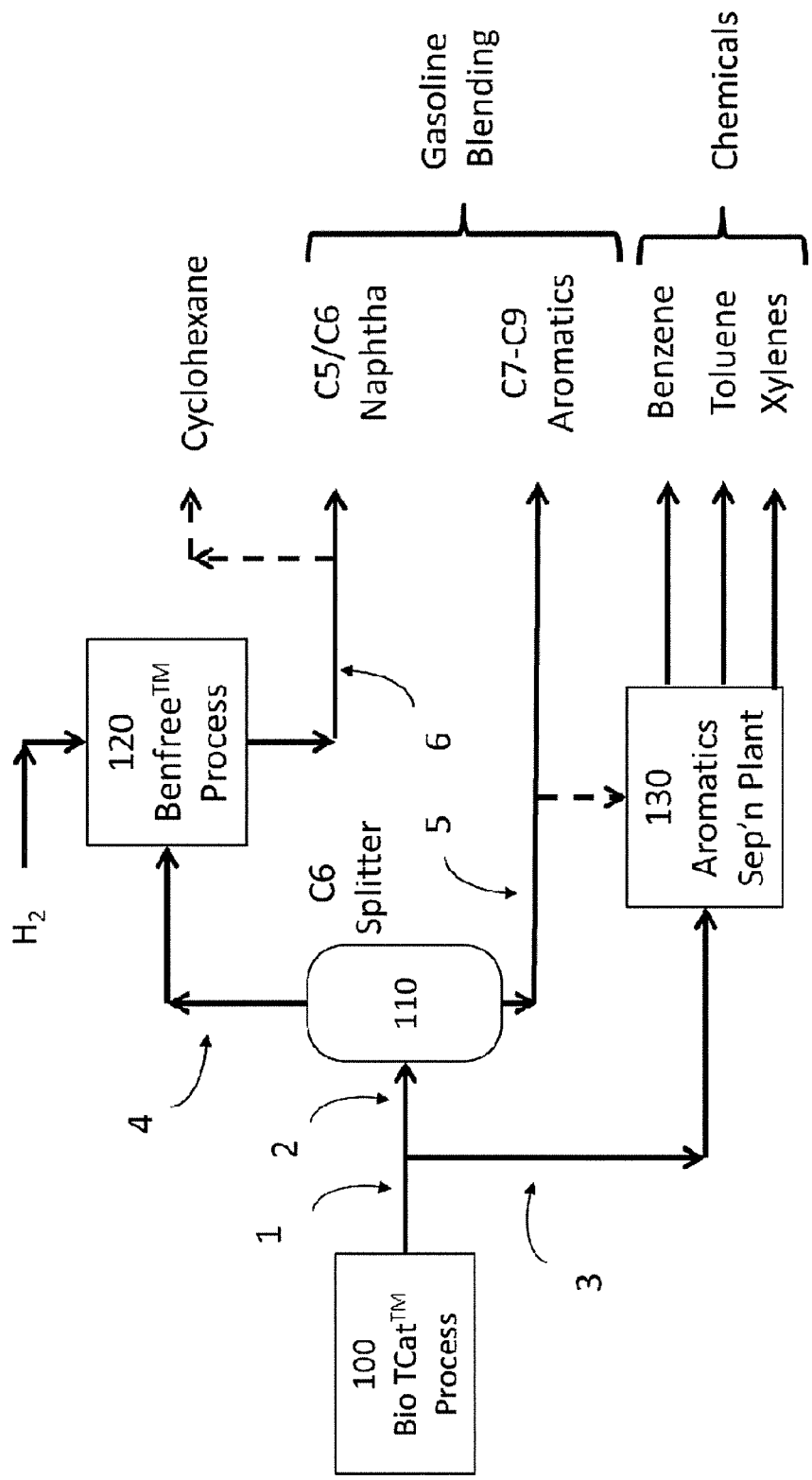
FIGS. 1, 2, 3 and 4 are block flow illustrations of embodiments of the present process.

As a result of extensive research in view of the above, we have found that we can economically and effectively conduct a CFP process to enhance manufacture of valuable fuel blendstock and chemical products by way of a series of sequential steps.

An embodiment of the present improved process comprises steps of: a) feeding biomass, such as, for example, that provided from renewable sources of organic materials, catalyst composition, such as comprising one or more crystalline molecular sieves, for example, those characterized by a SAR greater than 12 and a Constraint Index from 1 to 12, and transport fluid to a CFP process fluidized bed reactor maintained at reaction conditions, for example, a temperature from 300 to 1000° C. and pressure from 0.1 to 1.5 MPa, to manufacture a raw fluid product stream, b) feeding the raw fluid product stream of step a) to a solids separation and stripping system, hereinafter more particularly described, to produce separated solids and a fluid product stream, c) feeding the fluid product stream of step b) to a water or hydrocarbon quench vapor/liquid separation system, hereinafter more particularly described, to produce a liquid phase stream comprising components such as those selected from the group consisting of water, char, coke, ash, catalyst fines, oxygenates, and $C_9^+$ aromatics, and combinations thereof, and a vapor phase stream comprising carbon monoxide, carbon dioxide, hydrogen, olefins, and aromatics, said aromatics of the vapor phase stream selected from the group consisting of benzene, toluene, xylenes, phenols, naphthols, benzofuran, ethylbenzene, styrene, naphthalene, methylnaphthalene and combinations thereof, d) feeding the vapor phase stream of step c) to a condensation system, hereinafter more particularly described, to produce an organic phase stream, e) feeding the organic phase stream of step d) to a separation system to produce a high boiling fraction, such as one boiling at 185° C. and higher, and a low boiling fraction, such as one boiling below 185° C., f) hydrotreating at least a portion of the low boiling fraction, or a portion of the high boiling fraction, or both, of step e) at hydrotreating conditions to produce a hydrotreated fraction or fractions, and g) recovering fuel blendstock, such as gasoline blendstock, or diesel, or jet fuel, comprising less than 0.4 weight % olefins, less than 10 ppm by weight sulfur, less than 10 ppm by weight nitrogen, and less than 1 weight % oxygen, from the hydrotreated fraction of step f) in a product recovery system.

Embodiments of the invention include the novel fuel blendstocks recovered by step g) and mixtures thereof with fuels, such as gasoline, jet fuel, diesel fuel, or other fuel blendstocks, such as ethanol.

In one embodiment of the invention the fuel blendstock comprises at least 50, or at least 75, or at least 90, or from 50 to 99, or from 75 to 95% by weight hydrocarbons with from 5 to 16 carbon atoms. Another embodiment of the invention comprises the mixture of the above blendstock with petroleum derived materials in a jet fuel product. Another embodiment of the invention comprises a mixture of this renewable mixture with petroleum-derived materials such as jet fuel wherein the renewable mixture comprises from 0.1 to 50 volume % and jet fuel comprises from 50 to 99.9 volume % of the mixture.

In one embodiment of the invention the fuel blendstock comprises at least 50, or at least 75, or at least 90, or from 50 to 99, or from 75 to 95% by weight hydrocarbons with 9 or more carbon atoms. Another embodiment of the invention comprises the mixture of the above blendstock with petroleum-derived materials in a diesel fuel product. Another embodiment of the invention comprises a mixture of this renewable mixture with petroleum-derived materials such as diesel fuel wherein the renewable mixture comprises from 0.1 to 50 volume % and diesel fuel comprises from 50 to 99.9 volume % of the mixture.

An embodiment of the present improved process comprises steps of: i) feeding biomass, such as, for example, that provided from renewable sources of organic materials, catalyst composition, such as comprising one or more crystalline molecular sieves, for example, those characterized by a SAR greater than 12 and a CI from 1 to 12, and transport fluid to a CFP process fluidized bed reactor maintained reaction conditions, for example, a temperature from 300 to 1000° C. and pressure from 0.1 to 1.5 MPa, to manufacture a raw fluid product stream, ii) feeding the raw fluid product stream of step i) to a solids separation and stripping system, hereinafter more particularly described, to produce separated solids and a fluid product stream, iii) feeding the fluid product stream of step ii) to a quench vapor/liquid separation system, hereinafter more particularly described, utilizing water or hydrocarbon quench to produce a liquid phase stream comprising water, char, coke, ash, catalyst fines, oxygenates, and $C_9^+$ aromatics, and a vapor phase stream comprising carbon monoxide, carbon dioxide, hydrogen, olefins, and aromatics, said aromatics of the vapor phase stream selected from the group consisting of benzene, toluene, xylenes, phenols, naphthols, benzofuran, ethylbenzene, styrene, naphthalene, methylnaphthalene and combinations thereof, iv) feeding the vapor phase stream of step iii) to a condensation system, hereinafter more particularly described, to produce an organic phase stream, v) feeding the organic phase stream of step iv) to a separation system, hereinafter more particularly described, to produce a high boiling fraction, such as one boiling at 185° C. and higher, and a low boiling fraction, such as one boiling below 185° C., vi) feeding the low boiling fraction of step v) to a separation system, hereinafter more particularly described, to produce a fraction boiling above 85° C. and a fraction boiling below 85° C., vii) alkylating at least a portion of the fraction boiling below 85° C. of step vi) by contact with an alkylating agent at alkylating conditions to produce an alkylated fraction, or hydrogenating at least a portion of the fraction boiling below 85° C. of step vi) at hydrogenating conditions to produce a hydrogenated fraction, or both, and viii) recovering chemicals comprising ethylbenzene, cumene, propylbenzenes, linear alkylbenzenes wherein the alkyl chain comprises from 10 to 16 carbon atoms, or a combination thereof, from the alkylated fraction of step vii), or chemicals comprising cyclohexane from the hydrogenated fraction of step vii), or both, in a product recovery system.

As used herein, the terms "aromatics" or "aromatic compound" refer to a hydrocarbon compound or compounds comprising one or more aromatic groups such as, for example, single aromatic ring systems (e.g., benzyl, phenyl, etc.) and fused polycyclic aromatic ring systems (e.g., naphthyl, 1,2,3,4-tetrahydronaphthyl, etc.). Examples of aromatic compounds include, but are not limited to, benzene, toluene, indane, indene, 2-ethyltoluene, 3-ethyltoluene, 4-ethyltoluene, trimethylbenzene (e.g., 1,3,5-trimethylbenzene, 1,2,4-trimethylbenzene, 1,2,3-trimethylbenzene, etc.), ethylbenzene, styrene, cumene, n-propylbenzene, xylenes (e.g., p-xylene, m-xylene, o-xylene), naphthalene, methylnaphthalene (e.g., 1-methylnaphthalene), anthracene, 9,10-dimethylanthracene, pyrene, phenanthrene, dimethyl naphthalene (e.g., 1,5-dimethylnaphthalene, 1,6-dimethylnaphthalene, 2,5-dimethylnaphthalene, etc.), ethyl naphthalene, hydrindene, methylhydrindene, and dimethylhydrindene. Single ring and/or higher ring aromatics may also be produced in some embodiments. Aromatics also include single and multiple ring compounds that contain heteroatom substituents, i.e., phenol, cresol, benzofuran, aniline, indole, etc.

As used herein, the term "biomass" has its conventional meaning in the art and refers to any organic source of energy or chemicals that is renewable. Its major components can be: (1) trees (wood) and all other vegetation; (2) agricultural products and wastes (corn stover, fruit, garbage ensilage, etc.); (3) algae and other marine plants; (4) metabolic wastes (manure, sewage), and (5) cellulosic urban waste Examples of biomass materials are described, for example, in Huber, G. W. et al, "Synthesis of Transportation Fuels from Biomass: Chemistry, Catalysts, and Engineering," Chem. Rev. 106, (2006), pp. 4044-4098.

Biomass is conventionally defined as the living or recently dead biological material that can be converted for use as fuel or for industrial production. The criterion as biomass is that the material should be recently participating in the carbon cycle so that the release of carbon in the combustion process results in no net increase averaged over a reasonably short period of time (for this reason, fossil fuels such as peat, lignite and coal are not considered biomass by this definition as they contain carbon that has not participated in the carbon cycle for a long time so that their combustion results in a net increase in atmospheric carbon dioxide). Most commonly, biomass refers to plant matter grown for use as biofuel, but it also includes plant or animal matter used for production of fibers, chemicals or heat. Biomass may also include biodegradable wastes or byproducts that can be burned as fuel or converted to chemicals, including municipal wastes, green waste (the biodegradable waste comprised of garden or park waste, such as grass or flower cuttings and hedge trimmings), byproducts of farming including animal manures, food processing wastes, sewage sludge, and black liquor from wood pulp or algae. Biomass excludes organic material which has been transformed by geological processes into substances such as coal, oil shale or petroleum. Biomass is widely and typically grown from plants, including miscanthus, spurge, sunflower, switchgrass, hemp, corn (maize), poplar, willow, sugarcane, and oil palm (palm oil) with the roots, stems, leaves, seed husks and fruits all being potentially useful. Processing of the raw material for introduction to the processing unit may vary according to the needs of the unit and the form of the biomass. Biomass can be distinguished from fossil-derived carbon by the presence of 14C in amounts significantly above that found in fossil fuels.

Biomass used in the present process can most preferably be solid materials chosen from among wood, forestry waste, corn stover, and combinations thereof.

As used herein, the terms "olefin" or "olefin compound" (a.k.a. "alkenes") have their ordinary meaning in the art, and refer to any unsaturated hydrocarbon containing one or more pairs of carbon atoms linked by a double bond. Olefins include both cyclic and acyclic (aliphatic) olefins, in which the double bond is located between carbon atoms forming part of a cyclic (closed ring) or of an open chain grouping, respectively. In addition, olefins may include any suitable number of double bonds (e.g., monoolefins, diolefins, triolefins, etc.). Examples of olefin compounds include, but are not limited to, ethene, propene, allene (propadiene), 1-butene, 2-butene, isobutene (2-methylpropene), butadiene, and isoprene, among others. Examples of cyclic olefins include cyclopentene, cyclohexene, and cycloheptene, among others. Aromatic compounds such as toluene are not considered olefins; however, olefins that include aromatic moieties are considered olefins, for example, benzyl acrylate or styrene.

As used herein, the term "oxygenate" includes any organic compound that contains at least one atom of oxygen in its structure such as alcohols (e.g., methanol, ethanol, etc.), acids (e.g., acetic acid, propionic acid, etc.), aldehydes (e.g., formaldehyde, acetaldehyde, etc), esters (e.g., methyl acetate, ethyl acetate, etc.), ethers (e.g., dimethyl ether, diethyl ether, etc.), aromatics with oxygen containing substituents (e.g., phenol, cresol, benzoic acid etc.), cyclic ethers, acids, aldehydes, and esters (e.g. furan, furfural, etc.), and the like.

As used herein, the terms "pyrolysis" and "pyrolyzing" have their conventional meaning in the art and refer to the transformation of a compound, e.g., a solid hydrocarbonaceous material, into one or more other substances, e.g., volatile organic compounds, gases and coke, by heat, preferably without the addition of, or in the absence of, molecular oxygen, i.e. $O_2$. Preferably, the volume fraction of oxygen present in a pyrolysis reaction chamber is 0.5% or less. Pyrolysis may take place with or without the use of a catalyst. "Catalytic pyrolysis" refers to pyrolysis performed in the presence of a catalyst, and may involve steps as described in more detail below. Catalytic fast pyrolysis that involves the conversion of biomass in a catalytic fluid bed reactor to produce a mixture of aromatics, olefins, and a variety of other materials is a particularly beneficial pyrolysis process. Examples of catalytic pyrolysis processes are outlined, for example, in Huber, G. W. et al, "Synthesis of Transportation Fuels from Biomass: Chemistry, Catalysts, and Engineering," Chem. Rev. 106, (2006), pp. 4044-4098, incorporated herein by reference.

As used herein, the term "recovery" of a component is the fraction (or percent) of that component that is present in the recovered product stream(s) compared to the amount of that component that is present in the reactor effluent stream. For example if 10 grams of "A" is present in the reactor effluent and 8.5 grams of "A" is present in the recovered product stream, then the recovery of "A" is 8.5/10 or 0.85 (85%). All percentages provided herein are by mass unless otherwise indicated.

Catalyst components useful in the context of this invention can be selected from any catalyst known in the art, or as would be understood by those skilled in the art. Catalysts promote and/or effect reactions. Thus, as used herein, catalysts lower the activation energy (increase the rate) of a chemical process, and/or improve the distribution of products or intermediates in a chemical reaction (for example, a shape selective catalyst). Examples of reactions that can be catalyzed include: dehydration, dehydrogenation, isomerization, oligomerization, cracking, hydrogen transfer, aromatization, decarbonylation, decarboxylation, aldol condensation, molecular cracking and decomposition, combinations thereof, and other reactions. Catalyst components can be considered acidic, neutral or basic, as would be understood by those skilled in the art.

For catalytic fast pyrolysis, useful catalysts include those containing internal porosity selected according to pore size (e.g., mesoporous and pore sizes typically associated with zeolites), e.g., average pore sizes of less than 100 Angstroms (Å), less than 50 Å, less than 20 Å, less than 10 Å, less than 5 Å, or smaller. In some embodiments, catalysts with average pore sizes of from 5 Å to 100 Å may be used. In some embodiments, catalysts with average pore sizes of between 5.0 Å and 6.5 Å, or between 5.9 Å and 6.3 Å may be used. In some cases, catalysts with average pore sizes of between 7 Angstroms and 8 Å, or between 7.2 Å and 7.8 Å may be used.

The catalyst composition particularly advantageous in the CFP fluidized bed reactor of the present invention comprises a crystalline molecular sieve characterized by an SAR greater than 12 and a CI from 1 to 12. Non-limiting examples of these crystalline molecular sieves are those having the structure of ZSM-5, ZSM-11, ZSM-12, ZSM-22, ZSM-23, ZSM-35, ZSM-48, ZSM-50 or combinations thereof. As an embodiment, the catalyst composition comprises a crystalline molecular sieve characterized by an SAR from greater than 12 to 240 and a CI from 5 to 10, such as, for example, molecular sieves having the structure of ZSM-5, ZSM-11, ZSM-22, ZSM-23 or combinations thereof. The method by which CI is determined is described more fully in U.S. Pat. No. 4,029,716, incorporated by reference for details of the method.

The molecular sieve for use herein or the catalyst composition comprising same may be thermally treated at high temperatures. This thermal treatment is generally performed by heating at a temperature of at least 370° C. for a least 1 minute and generally not longer than 20 hours (typically in an oxygen containing atmosphere, preferably air). While subatmospheric pressure can be employed for the thermal treatment, atmospheric pressure is desired for reasons of convenience. The thermal treatment can be performed at a temperature up to about 925° C. The thermally treated product is particularly useful in the present process.

For the catalyst composition useful in this invention, the suitable molecular sieve may be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite, kieselguhr and combinations thereof. The relative proportion of suitable crystalline molecular sieve of the total catalyst composition may vary widely with the molecular sieve content ranging from 30 to 90 percent by weight and more usually in the range of 40 to 70 percent by weight of the composition. The catalyst composition may be in the form of an extrudate, beads or fluidizable microspheres.

The molecular sieve for use herein or the catalyst composition comprising it may have original cations replaced, in accordance with techniques well known in the art, at least in part, by ion exchange with hydrogen or hydrogen precursor cations and/or non-noble metal ions of Group VIII of the Periodic Table, i.e. nickel, iron and/or cobalt.

In embodiments that require hydrogen for hydrotreatment or hydrogenation, the required hydrogen can be separated from the product gases or generated from the product gases via the water gas shift reaction (WGSR), or from partial oxidation of product gases, or from gasification of one of several heavier product fractions.

$$CO + H_2O \rightarrow H_2 + CO_2 \qquad (1)$$

The key reaction of the WGSR process is depicted in equation (1). In the WGSR at least a portion of the carbon monoxide reacts with water to shift the equilibrium to produce hydrogen and carbon dioxide. The WGSR is an equilibrium limited reaction, and the formation of hydrogen is favored at lower temperatures. The reaction is generally conducted over a catalyst; there are high temperature (HT) catalysts, low temperature (LT) catalysts, and sulfur tolerant catalysts. Typical high temperature WGSR catalysts include iron-based catalysts such as zinc ferrite ($ZnFe_2O_4$), ferric oxide ($Fe_2O_3$), magnetite ($Fe_3O_4$), chromium oxides, and mixtures such as iron/chromia (90-95% $Fe_2O_3$ and 5-10% $Cr_2O_3$). The high temperature shift is usually conducted at 300-450° C. and pressures from 0.1 to 10 MPa (1 to 100 bar), although high pressure is not required. The pressure is usually dictated by the other unit operations in the process or the pressure at which the hydrogen is to be utilized. The shift catalysts employed at lower temperatures include copper promoted zinc oxide, copper promoted chromia, other catalysts with copper supported on metal oxides, and mixtures thereof. The LT WGSR process is conducted at 200-275° C. and 0.1 to 10 MPa. Low temperature shift catalysts are poisoned by sulfur and chlorine compounds, so often a guard bed of ZnO or other sulfur or halogen scavenger is used to remove traces of these impurities. For this reason sulfur tolerant WGSR catalysts based on Mo and Co have been developed for sulfur containing feeds. The water gas shift reaction is a highly exothermic equilibrium reaction and requires active control of the reactor temperature to produce the desired products.

In this invention, the gaseous product stream remaining after condensing the organic fraction in step d) or iv) comprises CO, $CO_2$, $H_2$, $CH_4$, light olefins, and traces of other materials. In order to produce hydrogen by the WGSR for use in the hydrotreatment or hydrogenation steps, the CO can be separated from the other components, although depending on the concentrations of these it may not be necessary. A typical product gas stream may comprise 30 to 60 volume % CO, 20 to 45% $CO_2$, 3 to 10% $CH_4$, 2 to 7% ethylene plus propylene, 0.2 to 5% hydrogen, and traces of other materials. Carbon dioxide inhibits the WGSR, so it can be removed in an amine scrubber or trapped with CaO or other absorbent. Olefins can be removed by hydrogenation to paraffins. After preliminary purification the CO stream can be mixed with steam and passed over a HT catalyst, a LT catalyst, or a series of HT and then LT catalysts to produce hydrogen. Lower temperatures favor hydrogen production so the typical exit temperature from the WGSR system is 180 to 220° C. for the LT process. The hydrogen produced from the WGSR process can be used in the hydrotreatment or hydrogenation processes of the invention.

Another route to produce hydrogen for the hydrotreatment or hydrogenation processes of the invention is the partial oxidation of the light hydrocarbons in the gaseous product stream from step d). In particular, the methane can be partially oxidized with molecular oxygen to produce a gaseous product comprising approximately a 2:1 mixture of hydrogen and carbon monoxide, although the gas mixture may be oxidized without separation or purification. The $H_2$ content of the mixture of $H_2$ and CO obtained from partial oxidation may be further increased in a WGSR step, or the product gas may be used for hydrotreatment or hydrogenation provided the activity of the chosen catalyst is not poisoned or inhibited by the presence of CO.

Yet another embodiment of the invention that utilizes hydrogen generated from byproducts of the catalytic fast pyrolysis for the hydrotreating or hydrogenation steps comprises the gasification of one or more of a variety of heavier product fractions. Gasification is well known in the art and it is practiced worldwide with application to solids and heavy liquid fossil fuels, including refinery bottoms. The gasification process of the invention uses partial oxidation to convert carbonaceous materials, such as $C_9^+$ products, oxygenates, char, coke, biofuel, or biomass with oxygen at high temperature, i.e., greater than 800° C., into synthesis gas (mixture of hydrogen and carbon monoxide), steam, and electricity. The synthesis gas comprising carbon monoxide and hydrogen can be enriched in hydrogen via the WGSR discussed previously, or utilized directly in a hydrotreating or hydrogenation process provided the catalyst is not sensitive to CO poisoning or inhibition.

In another embodiment of the invention, hydrogen recovered from within the inventive process such as by WGSR of CO, partial oxidation of hydrocarbons, or gasification of heavy materials, is utilized to hydrocrack one of the various heavy oxygenate, heavy aromatic, e.g. $C_9^+$, or the materials boiling above 185° C. recovered from steps e) or f) or elsewhere. In this embodiment the hydrocracked products may in part be returned to the catalytic pyrolysis reactor in step a) or may in part be combined with one of the fuel blendstocks.

Several embodiments of the invention are depicted in FIGS. 1, 2, 3, and 4, wherein process 100 is the Bio-TCat™ process. Examples of apparatus and process conditions suitable for the Bio-TCat™ process 100 are described in U.S. Pat. Nos. 8,277,643, 8,864,984, and 9,169,442, and United States Patent Publications 2014/0027265 A1, 2014/0303414 A1 and 2013/0060070A1, each incorporated herein by reference. Conditions for Bio-TCat™ conversion of biomass may include one or a combination of the following features (which are not intended to limit the broader aspects of the invention): biomass treatment, a catalyst composition; that catalyst composition optionally comprising a metal; a fluidized bed, circulating bed, moving bed, or riser reactor; a fluidizing fluid; an operating temperature in the range of 300 to 1000° C. and a pressure in the range of 0.1 to 3.0 MPa (1 to 30 atm); and a solid catalyst/biomass mass ratio of from 0.1 and 40. Solid biomass may be fed to the reactor in a continuous or intermittent fashion. Solid catalyst may be regenerated in an oxidative process and in part returned to the reactor. Solid catalyst may be removed from the reactor, stripped with steam to displace organic materials and reactive gases, and then regenerated in a fluid bed catalyst regenerator by treatment with an oxygen containing gas, and in part returned to the reactor. To reduce the fraction of non-aromatic components in the products, and thereby benefit downstream separation and conversion technologies, the reaction severity in the Bio-TCat™ reactor can be increased. Methods to achieve greater reaction severity include higher reaction temperature, higher catalyst activity which can be achieved by higher fresh catalyst makeup and spent catalyst removal rates, or by changes to the catalyst (e.g. higher zeolite content, lower silica/alumina ratio, greater macro and meso-porosity, etc), higher pressure, or longer residence time.

Biomass may not be available in a convenient form for processing in the fluid bed reactor of the Bio-TCat™ process. While solid biomass is the preferred feed, the solid biomass may comprise portions of liquids at ambient conditions. Solid biomass may be treated in any of a number of ways to make it more suitable for processing including cutting, chopping, chipping, shredding, pulverizing, grinding, sizing, drying, roasting, torrefying, washing, extracting, or some combination of these in any order to achieve the desired properties of the biomass feed as to size, moisture, sulfur and nitrogen impurities content, density, and metals content. Procedures to inhibit biomass clumping and agglomeration may be employed.

Following conversion in the fluid bed reactor, the products of Bio-TCat™ process 100 are recovered by a combination of solids separation, water or hydrocarbon quenching, gas-liquid separation, compression cooling, gas-liquid absorption, condensation of condensable compounds, or other methods known in the art, to produce a mixture of $C_4^+$ hydrocarbons including species having boiling points above those of gasoline or on-road diesel fuels. Distillation can be used to separate out the desirable $C_5$-$C_9$ cut. This product can them be subject to mild hydrotreatment to remove heteroatoms and reduce the dienes, vinyl-aromatics, and olefins present as contaminants, and provide a first liquid stream. Alternatively a Bio-TCat™ product having a broader boiling range than $C_5$-$C_9$ (e.g. $C_4$-$C_{12}$ or higher) can be hydrotreated first prior to distillation to recover the $C_5$-$C_9$ fraction.

The $C_5$-$C_9$ aromatics-rich liquid product that is produced by the catalytic pyrolysis of biomass material over a zeolite catalyst is called "AnelloMate". The aromatic concentration in AnelloMate is extremely high compared to current petroleum-based processes that make aromatics, such as naphtha reforming and steam cracker pyrolysis gasolines. This is believed to be a consequence of the reaction chemistry, the high reaction severity, and the selectivity that the catalytic fast pyrolysis catalyst has for aromatics at the expense of non-aromatic species such as paraffins, olefins, and dienes. The high concentration of aromatics is advantageous in subsequent, downstream separation and conversion processes.

After recovery and separation from solids, by-product water, light gases, and heavy $C_{10}^+$ hydrocarbons and oxygenates, the AnelloMate naphtha-range product is subject to mild hydrotreating to remove the relatively low levels of organo-sulfur and organo-nitrogen compounds, and oxygenates that are co-produced in trace amounts by the pyrolysis process. The mild hydrotreating step reduces the amount of heteroatom-containing hydrocarbons in the product to less than 1 ppm each. Mild hydrotreating may also hydrogenate undesirable dienes, vinyl-aromatics, and olefins to their saturated analogs, but the saturation of aromatic rings is avoided to prevent unnecessary hydrogen consumption and loss of gasoline octane rating that occurs when aromatic rings are saturated to their corresponding naphthenic rings. The hydrotreatment may be conducted by contacting the liquid with a hydrogen-containing gas at a pressure from 0.1 MPa to 40 MPa (1 to 400 atm), preferably 0.2 to 2 MPa (2 to 20 atm), at a temperature from 40 to 350° C., preferably from 40 to 250° C., liquid hourly space velocity of 0.1 to 19 hr-1, preferably 1 to 4 hr-1, gas to liquid ratio of 1 to 25 m3/m3, preferably 5 to 20 m3/m3, in the presence of a solid catalyst. The hydrogen-containing gas may comprise at least 90%, or at least 95%, or at least 98% H2. Solid catalysts useful for the hydrotreating process step include Ni, Co, Fe, Cu, Zn, Ag, Pt, Pd, Ru, Rh, Ir, Mo, W, or combinations thereof, deposited on oxide supports including oxides of Al, Si, Ti, Zr, Th, Mg, Ca, or some combination of these, either as crystalline solids or as amorphous mixtures. In some cases the catalyst may comprise chlorinated alumina, a zeolite, active carbon, clays, aluminous cements, rare earth oxides, or alkaline-earth oxides. The hydrotreatment can be carried out in a fixed bed, trickle bed, catalytic distillation reactor, or fluid bed reactor, with counter- or co-current flow of feed and $H_2$. To control the exothermic heat of reaction, reactor vessels may be designed to contain several separate beds of catalyst having liquid and gas distributors or re-distributors between them. Under these conditions the majority of heteroatom compounds are converted to hydrocarbons and the heteroatoms are rejected as $H_2S$, $NH_3$, or water. Suitable conditions and operation of distillation reactors are described in U.S. Pat. No. 8,808,533, and United States Patent Publication 2010/0063334, incorporated herein by reference. Products from the hydrotreating reactor are cooled to 40° C. and the pressure is reduced to 2.3 MPa (23 atm) before being discharged into a high pressure separator flash drum. In the drum, the hydrogen-rich gas is separated from the liquid product. Hydrogen-containing off-gas from the separator is sent to the recycle gas compressor which is used to circulate hydrogen back to the reactor. A slip stream containing excess hydrogen and the light gas products from the hydrotreating reactions is removed, and is either re-processed to remove the contaminants in it (e.g. water, $H_2S$, $NH_3$, etc) or used downstream in the benzene saturation reactor. The liquid product from the high pressure separator contains some dissolved light gases that are removed downstream in the main fractionator.

The hydrotreated products are separated into a heavy $C_{10}^+$ fraction and a $C_5$-$C_9$ fraction in a packed or trayed tower that operates at about 0.36 MPa (3.6 atm) pressure, contains about 25 theoretical stages, an overhead condenser operating at about 40° C., and a bottom reboiler operating at about 264° C. Feed is pre-heated in the main fractionator feed heater to 150° C. and fed to the column on an intermediate tray. The overhead recycle ratio can be 2.5 by mass. The distillate product contains the full-range $C_5$-$C_9$ AnelloMate product, and the bottoms product contains a $C_{10}^+$ heavy fraction. A small amount of waste gas is generated and removed from the overhead condenser accumulation drum.

Figure 2:
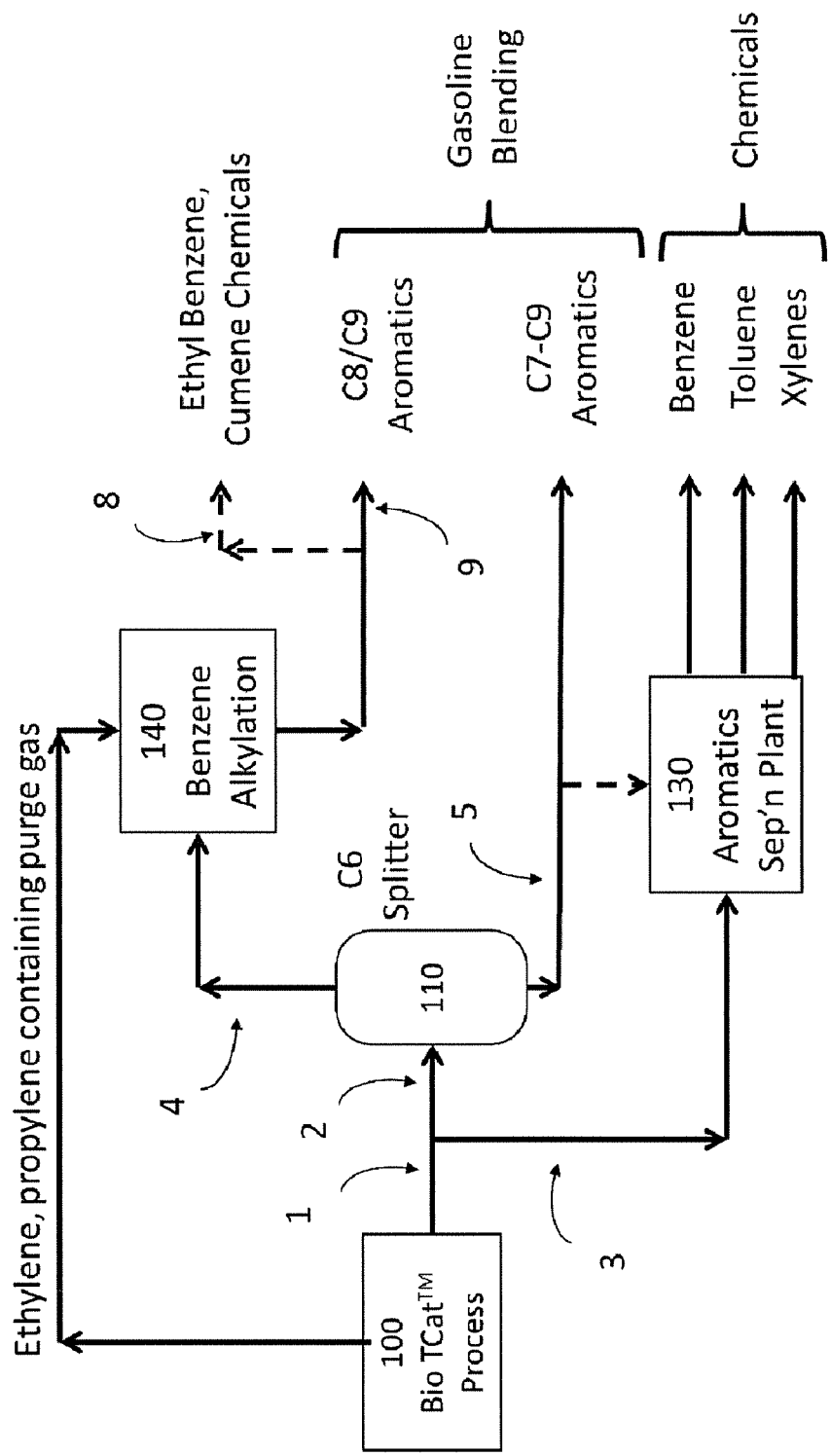
Figure 3:
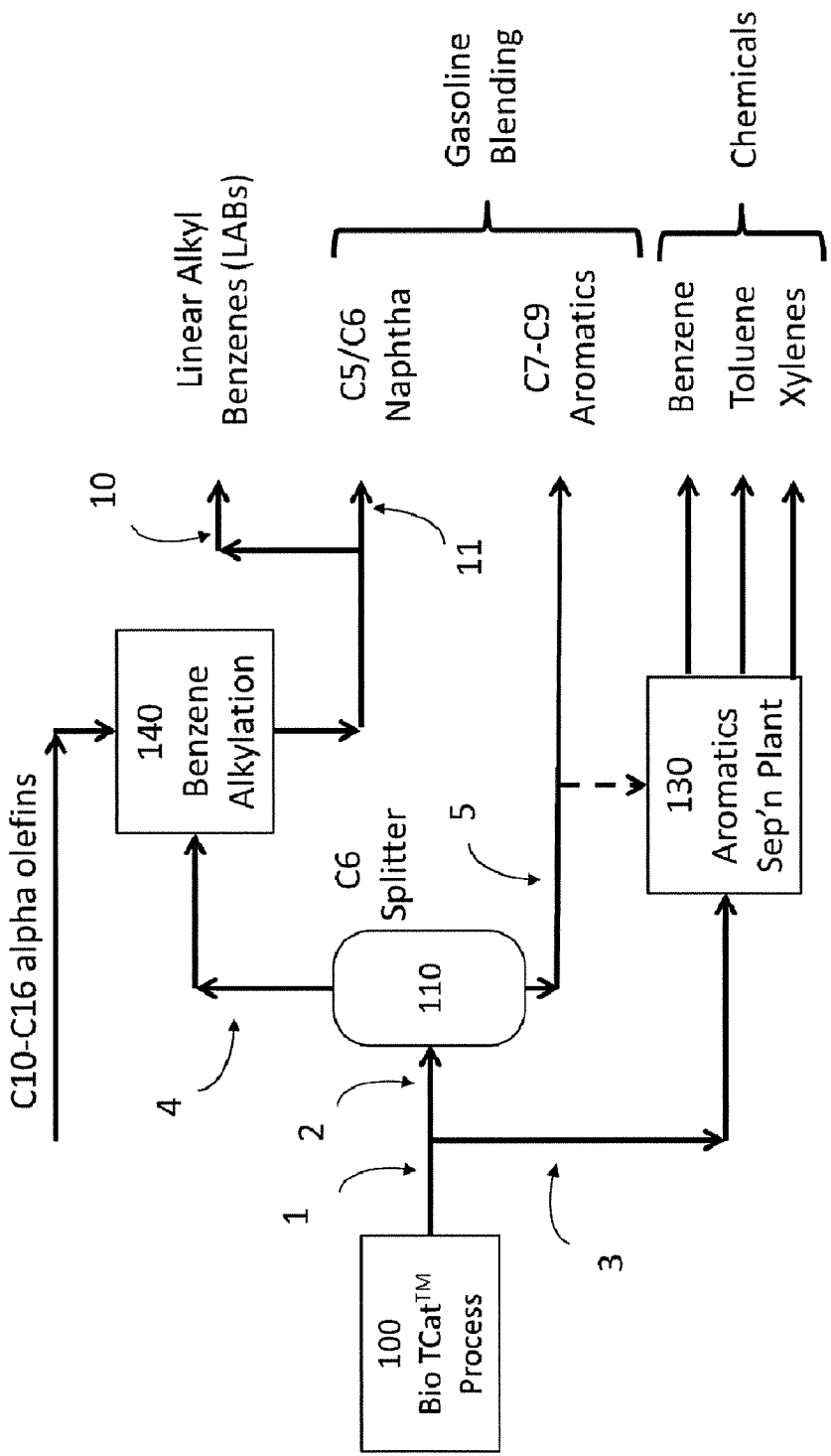
Figure 4:
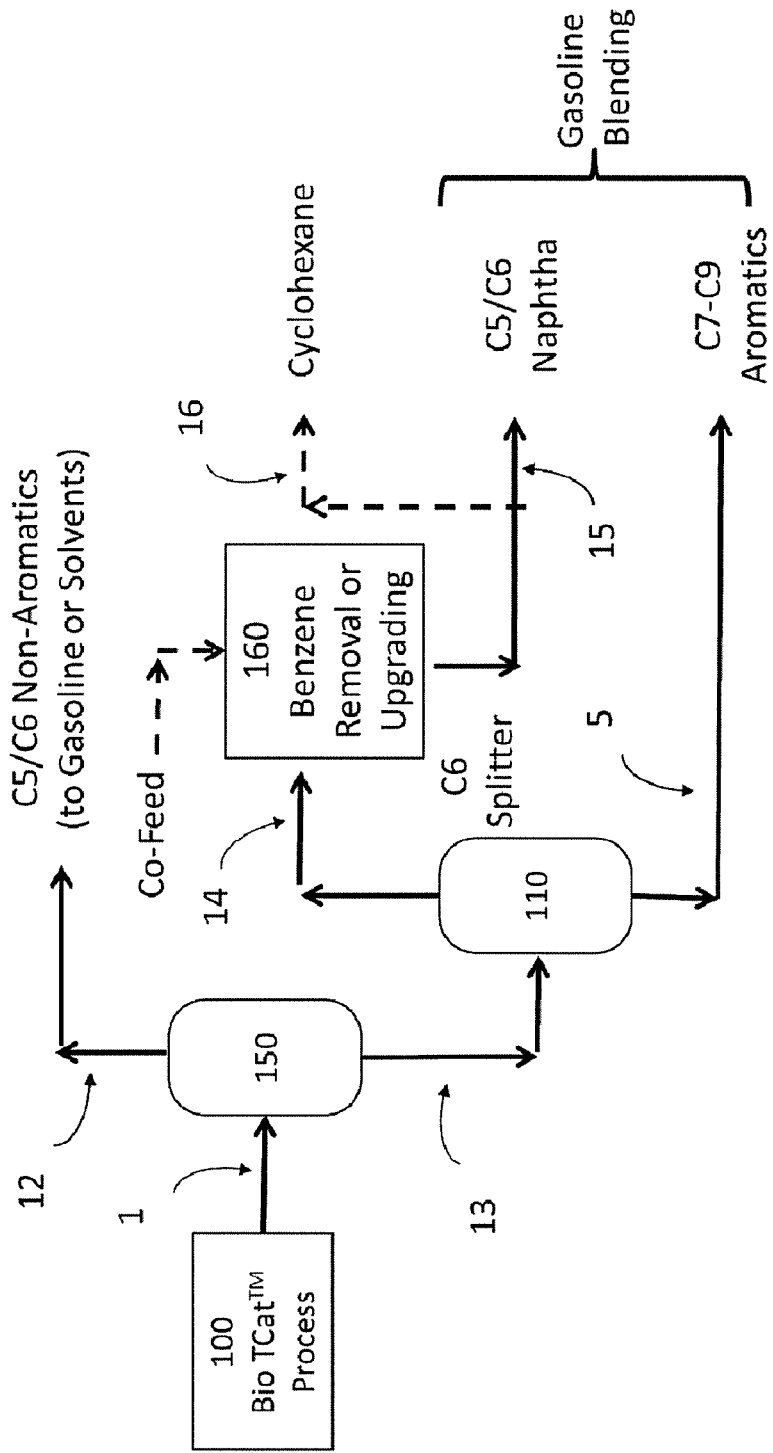

In some embodiments, a $C_6$ splitter is introduced into the processing of the hydrotreated Bio-TCat™ product to improve product separation and recovery and permit production of useful fuel blendstocks and chemicals. By introducing a $C_6$ splitter into the process, the majority of benzene can be separated and processed by a variety of means including: benzene saturation with hydrogen, as shown in FIG. 1, benzene alkylation with low molecular weight olefins, either produced by the Bio-TCat™ process or fed from a separate source, as shown in FIG. 2, benzene conversion to linear alkyl benzenes by alkylation with $C_{10}$-$C_{16}$ alpha-olefins, as shown in FIG. 3, or benzene recovery as a high purity stream that can be used for various processes, as shown in FIG. 4.

As shown in FIG. 1, hydrotreated full-range AnelloMate $C_5$-$C_9$ product stream 2 can be separated by distillation or other means into a second liquid distillate stream 4 that comprises $C_5$-$C_6$ naphtha, benzene, and other low boiling components, and a third liquid bottoms stream 5 that comprises $C_7^+$ materials including toluene, xylenes, trimethylbenzenes, and other higher boiling components but which has a very low benzene concentration. The amount of benzene in the third liquid stream 5 comprising $C_7^+$ materials can be controlled by the design of the distillation tower, such as by the number of trays or height of packing material used in the tower to effect separation, or by distillation tower operation, or both. Similarly the amount of toluene in the second liquid stream 4 comprising $C_5$-$C_6$ naphtha can be controlled in the same manner. Preferably the distillation of stream 2 into two fractions can be conducted so that materials with normal boiling points below about 85° C. are collected overhead and those materials with normal boiling points above about 85° C. are collected in the column bottoms. The reflux ratio, which is the amount of overhead material returned to the column divided by the amount of overhead product withdrawn from the tower, is an operating parameter that can be used to control the concentration of benzene in the bottom product. The naphtha distillate product stream 4 can comprise at least 85, or at least 90, or at least 94, or from 85 to 99.9, or from 90 to 99% benzene by weight. The naphtha distillate product stream 4 can have a toluene concentration less than 5%, or less than 2%, or less than 1%, or less than 0.5, or less than 0.2, or from 0.01 to 5, or from 0.01 to 1% by weight. The $C_7^+$ bottom product stream 5 can have a benzene concentration less than 5, or less than 2, or less than 1, or less than 0.5, or less than 0.2, or from 0.01 to 5, or from 0.01 to 1% by weight. The $C_7^+$ stream 5 can be further separated into a toluene stream comprising at least 90%, or at least 95%, or at least 99.5% toluene, or a xylenes stream comprising at least 90%, or at least 95%, or at least 99.5% xylenes by weight, or both.

As depicted in FIG. 1, after separation of the $C_7^+$ materials, the stream 4 is optionally routed to a benzene saturation reactor where the benzene in the stream is saturated by hydrogen in the presence of a catalyst and converted with near 100% selectivity to cyclohexane in a stream 6. The composition of stream 6 can be at least 85%, or at least 90%, or at least 95%, or at least 99% cyclohexane. The benzene-depleted light naphtha of stream 6 can then be blended into gasoline, or optionally used as a feedstock in a cyclohexane conversion process such as for oxidation to cyclohexanol, cyclohexanone, or both, which is a step in the upgrading sequence leading to Nylon manufacture. One commercial benzene saturation process 120 that could be used to treat the Bio-TCat™ light naphtha 4 is the BenFree™ process licensed by Axens. Stream 5 comprising toluene and xylenes can be used in a blend stock or can optionally be sent to an aromatics separation process 130, as shown in FIG. 1, to produce purified chemical feedstocks. A portion of the benzene-depleted light naphtha of stream 6 can be combined with a portion of stream 5 that comprises toluene and xylenes in any proportion that comprises at least 1% by volume of the benzene-depleted stream and at least 1% by volume of the toluene-containing stream to form a gasoline blendstock.

Alternatively, the benzene-rich light naphtha stream 4 can be used as feedstock in a benzene conversion and functionalization step to make useful chemicals, or benzene can be converted or removed to provide a fuel blendstock having lower benzene content. FIG. 2 presents a conceptual block flow diagram of a process of the invention for producing gasoline blendstocks and chemicals that includes the alkylation of benzene with light olefins. As shown in FIG. 2, after separation the benzene-rich light naphtha stream 4 can be alkylated with either ethylene, propylene, or a mixture of $C_2$-$C_4$ olefins in the presence of an alkylation catalyst in a benzene alkylation unit 140 to make ethylbenzene, propylbenzenes (e.g. 1-, or 2-propylbenzene), or both, which can be blended into gasoline, stream 9, or optionally upgraded to a variety of chemicals stream 8. Ethylbenzene or propylbenzene streams of at least 85% or at least 90%, or at least 95% by weight ethylbenzene or propylbenzenes or both can be obtained by further separation by distillation or other conventional separation processes. Optionally, the ethylbenzene can be upgraded by dehydrogenation to styrene, and polymerization of the styrene to make polymers. Optionally, cumene can be separated from the alkylated benzene stream and provided to an oxidation process to prepare phenol and acetone. The olefins used for the alkylation can be olefins recovered from the products of the Bio-TCat™ process. Any $C_5$-$C_7$ non-aromatics present in the original naphtha can also be blended into gasoline, and thus no pre- or post-purification of the alkylated product is needed for a fuels application. Stream 5 comprising toluene and xylenes can be used in a blend stock or can optionally be sent to an aromatics separation process 130, as shown in FIG. 2.

FIG. 3 presents a conceptual block flow diagram of an embodiment of the invention for producing gasoline blendstocks and chemicals that includes the alkylation of benzene with $C_{10}$-$C_{16}$ linear alpha olefins to produce linear alkyl benzenes (LABs). LABs are intermediates in the production of surfactants for use in detergents, particularly biodegradable detergents. As shown in FIG. 3, after separation the benzene-rich light naphtha stream 4 can be alkylated with a mixture of $C_{10}$-$C_{16}$ alpha olefins in a benzene alkylation unit 140 to make linear alkyl-benzenes which can be separated into a light $C_5$/$C_6$ material to be blended into gasoline, stream 11, and a mixture of LABs, stream 10. The mixture of LABs can comprise a mixture wherein at least 75%, or at least 85%, or at least 95%, or at least 99% of the linear alkyl benzenes comprise materials with molecular weight from 218 to 302 grams per mole. Optionally, the LABs stream 10, or some fraction thereof, can be sulfonated with SO3 or its equivalent to produce linear alkylbenzene sulfonates. Any $C_5$-$C_7$ non-aromatics present in the original naphtha can also be blended into gasoline, and thus no pre- or post-purification of the alkylated product is needed for a fuels application. Stream 5 comprising toluene and xylenes can be used in a blendstock or can optionally be sent to an aromatics separation process 130, as shown in FIG. 3.

FIG. 4 presents a conceptual block flow diagram of an embodiment of the invention for producing gasoline blendstocks and chemicals that includes the separation of light naphtha low boiling materials and dissolved gases from the lightly hydrotreated $C_5$-$C_9$ products, stream 1, of the Bio-TCat™ process 100. In FIG. 4 a stabilizer column 150 ("de-hexanizer") is placed before the $C_6$ splitter 110. The de-hexanizer column removes some of the lighter $C_1$-$C_6$ paraffins, stream 12, in the Bio-TCat™ $C_5$-$C_9$ product, prior to separation of the benzene. Separation of the higher boiling stream 13 in the de-hexanizer 150 results in a higher purity benzene stream 14 from the $C_6$ splitter 110 overhead. The de-hexanizer 150 is designed to separate compounds with normal boiling points below 75° C. into the overhead stream 12, and recover compounds with normal boiling points above 75° C. in stream 13. As shown in FIG. 4, the benzene-rich stream 14 can be removed by distillation to provide a low benzene naphtha stream 5 and a high purity benzene stream 14 that can be upgraded in unit 160 operation by hydrogenation to cyclohexane 16 or by an alkylation process (not shown) as presented in FIG. 2 or 3.

Another option to produce additional renewable blending materials that may be favored when renewable materials command a premium value, is to hydrogenate a portion of the mixed aromatic stream, either streams 1, 3, or 5 in FIGS. 1, 2, 3, and 4. The hydrogenation of the mixed aromatics can be performed in a manner similar to the hydrotreatment described above, except the conditions for saturating aromatics are generally more severe than for hydrogenating olefins. The temperature of the aromatics hydrogenation may be between 300 and 450° C., pressures of 1.5 to 5.5 MPa (15 to 55 bar gauge), liquid hourly space velocities of 0.5 to 5 hr-1, hydrogen partial pressures of 0.5 to 3.0 MPa (5 to 30 bar), and total hydrogen circulation rates of 25 to 350 $nm^3$ of $H_2$ per $m^3$ of feed. Catalyst can be of the conventional types used for naphtha pre-treating processes with petroleum fractions (e.g. cobalt/molybdenum on alumina, nickel/molybdenum on alumina, nickel/tungsten, etc). Recovery of the products of the hydrogenation of the mixed aromatics may produce a product mixture consisting of compounds chosen from among the cyclohexanes including cyclohexane, and methyl-, dimethyl-, ethyl, methyl-ethyl- or propyl-alkylated cyclohexanes, or other multiply alkylated cyclohexanes.

Figure 5:
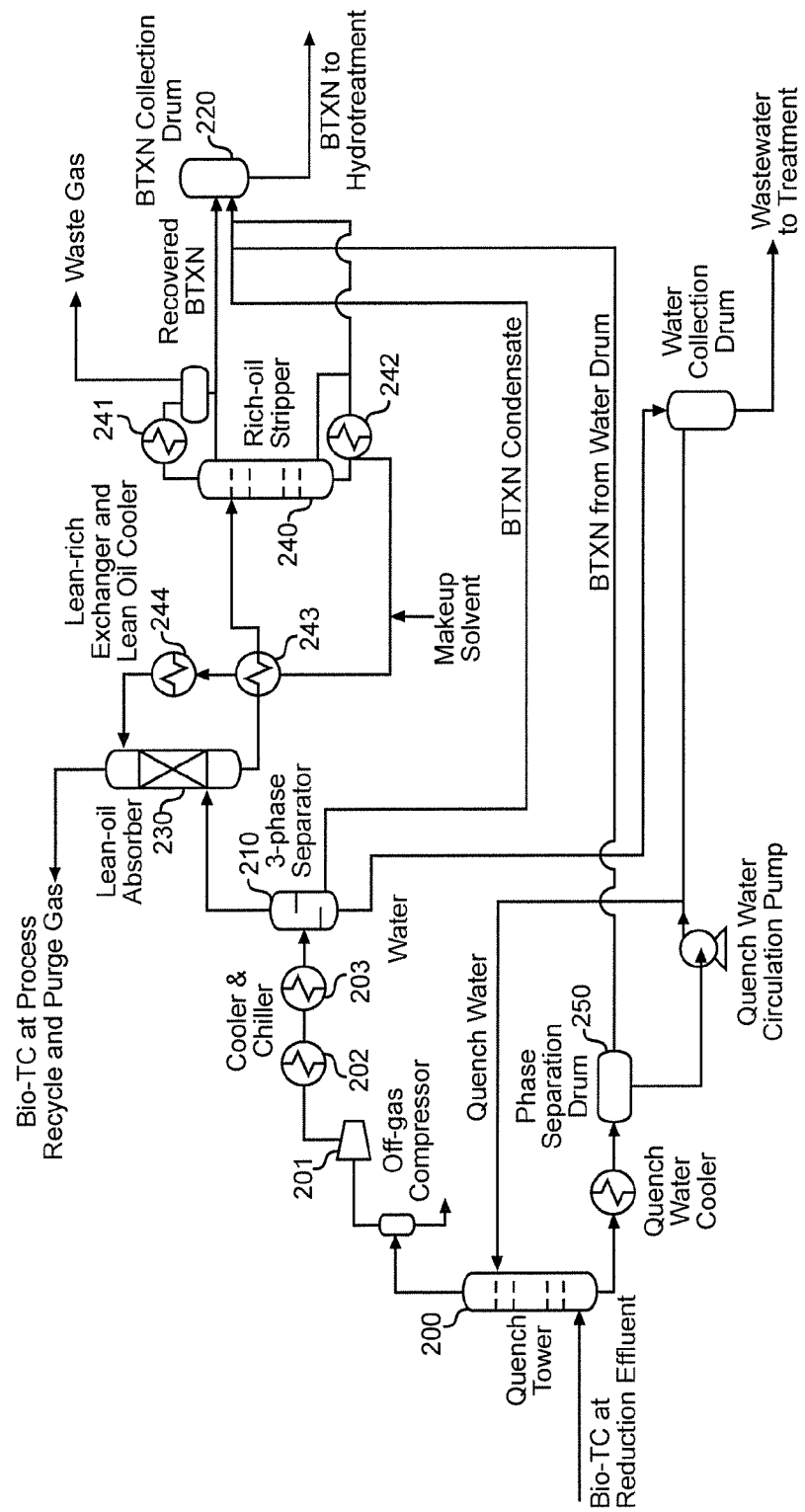
FIGS. 5, 6 and 7 are block flow illustrations of various unit operations of the present process.
Figure 6:
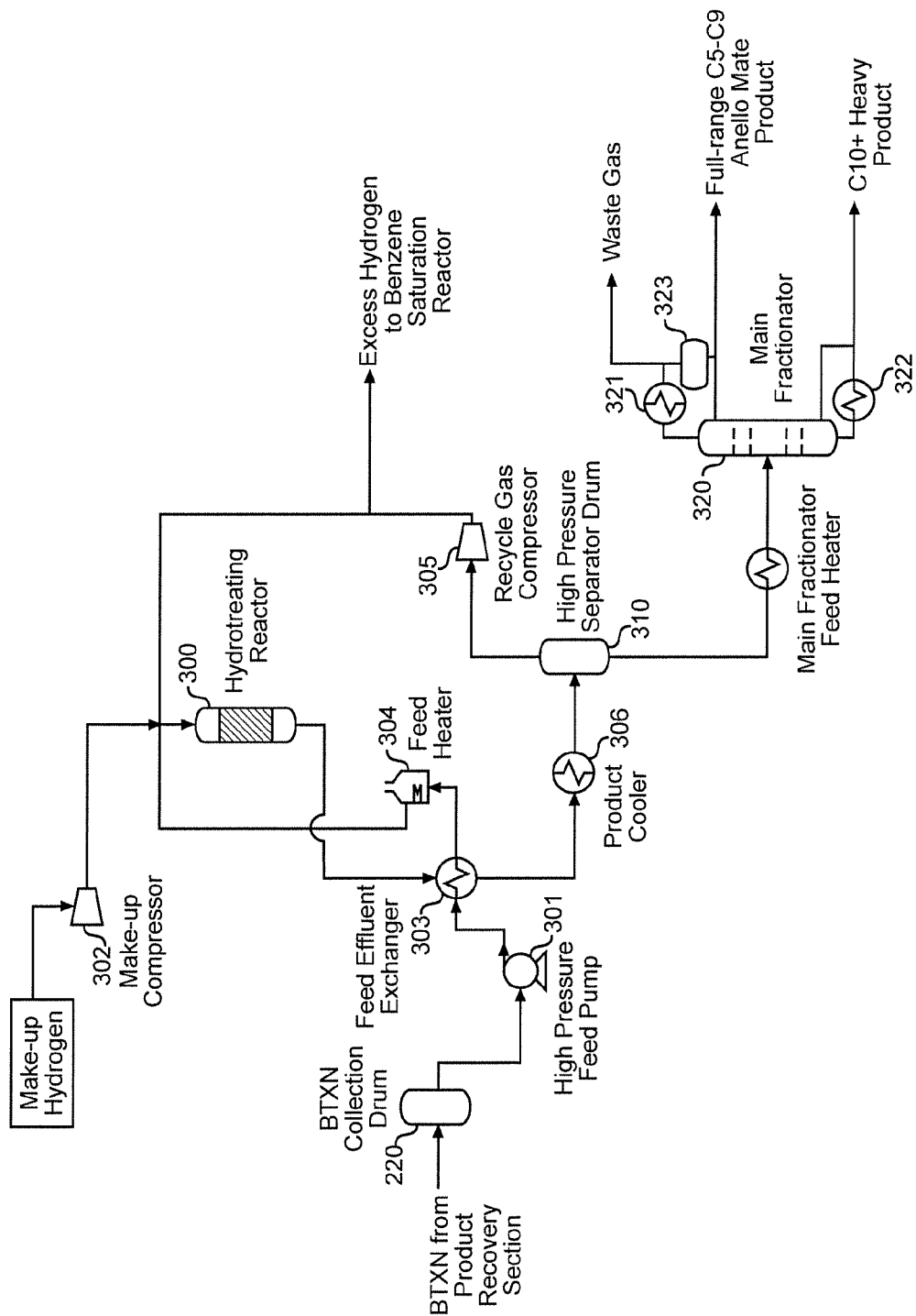
Figure 7:
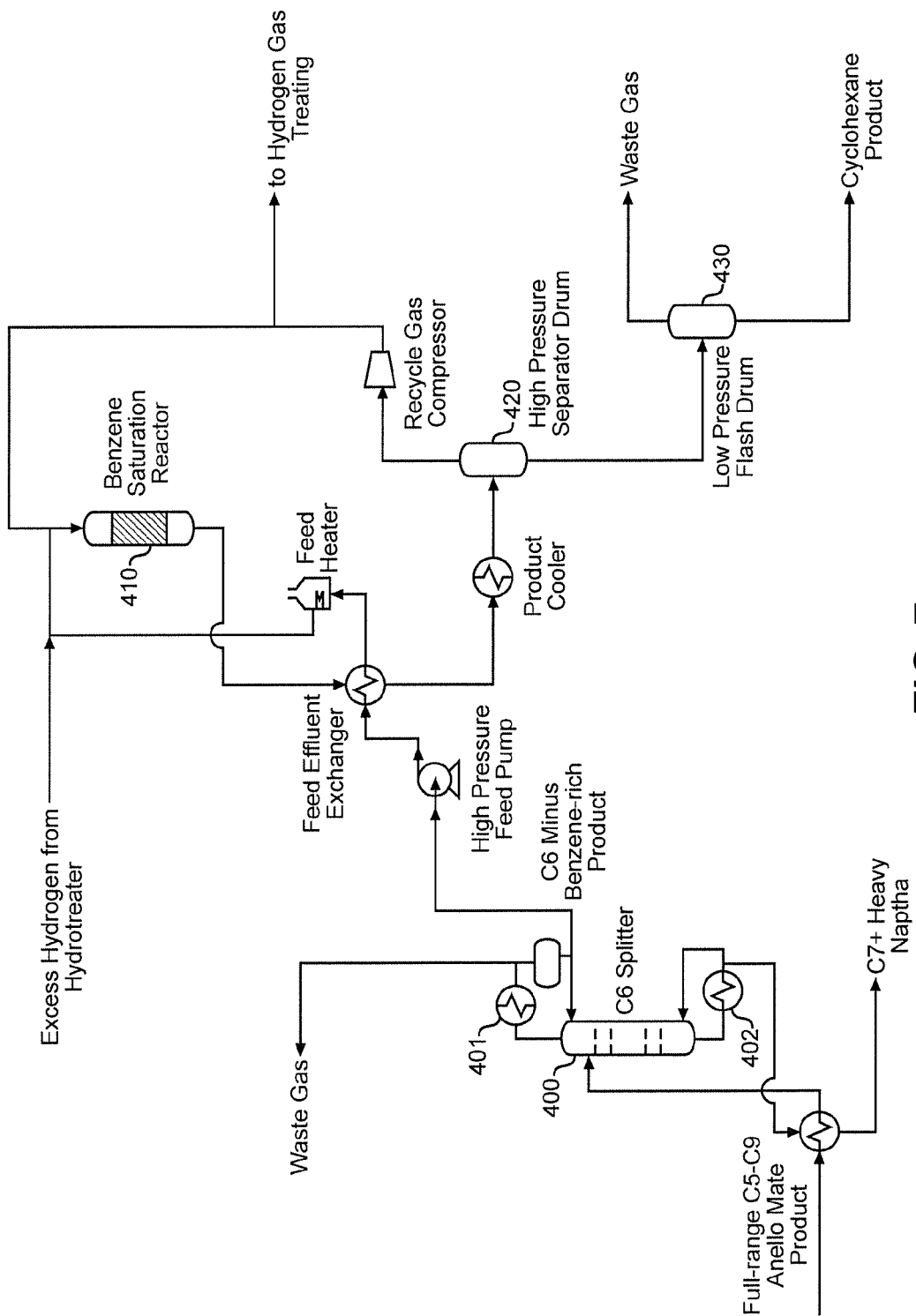

Downstream recovery and purification of the reactor effluent was modeled using the Aspen Plus™ process simulation software package. FIGS. 5-7 show process flow diagrams for the process. These process flow diagrams represent preliminary optimizations for minimal capital and operating costs, and for other common engineering practices such as heat and energy integration. Using conventional engineering practices, one skilled in the art could accomplish further cost and energy optimization based on the designs presented herein.

As shown in FIG. 5, hot reaction product vapors at 3.2 barg pressure (0.42 MPa absolute pressure) exit the Bio T-Cat™ reactor and may be cooled from 575° C. to 475° C. in a heat exchanger (not shown in FIG. 5). The cooling can be facilitated by steam generation on the cold side of the exchanger. The hot product from the exchanger is sent to a water quench tower 200 where the vapors are cooled to about 75° C., optionally using water that is produced by the Bio-TCat™ process. The quench tower in the model contains four theoretical trays, although this can be optimized to provide the desired separation. Most of the hydrocarbons exit with the quench tower overhead vapors. The overhead vapors are compressed in compressor 201 to over 8 bar gauge (0.9 MPa) and cooled to 5° C. in a heat exchanger 202 and chiller 203. Various types of commercially available industrial chilling units can be used to accomplish this. At this temperature and pressure, a substantial amount of $C_5$-$C_{12}$ hydrocarbons are condensed along with some water. The hydrocarbon and water separate into a hydrocarbon-rich upper layer and a water-rich lower layer in the 3-phase separation drum 210. The hydrocarbon-rich liquid product is sent downstream to the BTXN collection drum 220 prior to hydrotreating for removal of sulfur, nitrogen, and oxygen impurities.

There is still recoverable hydrocarbon in the off-gas stream exiting the 3-phase separator. This stream is contacted with heavy diesel oil (e.g. "lean oil") in a gas-liquid absorber tower (e.g. "lean oil absorber") 230. Hydrocarbons in the vapor phase are transferred to the liquid, and a negligible amount of diesel is lost to the vapor phase. The oil exiting the bottom of the absorber contains much of the hydrocarbon that entered as vapor, and thus this oil is referred to as "rich oil". The absorber column 230 is either a packed or trayed contactor modeled with 7 theoretical trays and operating at 7 barg (0.8 MPa). The top tray of the absorber operates at about 35° C., due to the hot incoming lean oil, but the lower sections of the tower are cooler due to the large amount of low temperature product gas passing through the tower. Conventional petroleum-sourced diesel, or renewable bio-diesel, or a by-product stream of the process can be used as the oil.

Light hydrocarbons in the rich oil are recovered in a rich oil stripper 240. This is a 20 theoretical stage packed or trayed tower with a reboiler 242 and overhead condenser 241. The tower 240 operates at about 2 barg (0.3 MPa) pressure, and rich oil feed enters the tower at stage 5. A recycle ratio of 2:1 by mass is used to control the overhead temperature of the column to about 130° C. The overhead condenser 241 return temperature is 40° C. and the reboiler 242 temperature is 329° C. The overhead liquid distillate product is rich in BTX hydrocarbons. These are also sent to the BTXN collection drum 220. The bottoms product from the rich oil stripper is substantially free of BTXN components. It is cooled to 100° C. and recycled to the lean oil absorber 230 in a continuous process or is optionally in part sent to a separate collection drum (not shown). An absorber and rich oil stripper feed-effluent heat exchanger 243 and a lean oil cooler 244 are used to adjust the temperature of the lean oil being fed to the absorber.

The quench tower bottoms product exits the tower around 115° C. and 3.3 bar gauge (0.43 MPa) pressure. This liquid product is cooled to 40° C. and sent to a phase separation drum 250. Any hydrocarbons that form a light upper liquid phase are removed and sent to the BTXN collection drum 220 or to a separate product collection drum. A large amount of cooled water is recycled back to the top of the quench tower where it is used to remove the heat contained in the Bio-TCat™ reactor effluent. Alternatively, the product recovery section could be designed to use some of the BTXN product as a liquid quench medium for the quench tower instead of water. In this case, the predominant liquid exiting the phase separation drum would be hydrocarbon, and the water product and moisture would be removed as a lower liquid phase.

FIG. 6 is a process flow diagram for the hydrotreating reactor (HDT) and the main fractionator. The HDT reactor uses hydrogen to convert heteroatom containing organic compounds to their corresponding hydrocarbon products. The main fractionator is used to separate out $C_4$ to $C_9$ or $C_5$ to $C_9$ hydrocarbon product from heavy $C_{10}^+$ products such as indane, indene, naphthalene, and other multi-ring compounds.

The collected BTXN product described in FIG. 5 is pumped to 25.5 bar gauge (2.6 MPa) by the feed pump 301. Makeup hydrogen at 98% purity (remainder is carbon monoxide) is used as fresh hydrogen makeup to the HDT reactor. A compressor 302 is used to elevate the hydrogen pressure to match reaction conditions. The untreated liquid BTXN product is heated in a feed-effluent exchanger 303 and then a heater 304 to come to typical hydrotreating temperatures (see below). The heater can use any suitable method including exchange with a hotter fluid, or in a fired heater that uses a fuel such as natural gas or one of the high-BTU waste gases generated by the Bio-TCat™ process or its downstream recovery sections.

In the hydrotreating reactor 300, trace levels of organo-sulfur, nitrogen, and oxygen compounds are removed by reaction with hydrogen. Conditions in the reactor are temperatures between 300 and 350° C., pressures of 15 to 55 bar gauge (1.6 to 5.6 MPa), liquid hourly space velocities of 0.5 to 5 hr-1, hydrogen partial pressures of 5 to 30 bar (0.5 to 3.0 MPa), and total hydrogen circulation rates of 25 to 350 nm3 of H2 per m3 of liquid feed. Catalyst can be of the conventional types used for naphtha pre-treating processes with petroleum fractions (e.g. cobalt/molybdenum on alumina, nickel/molybdenum on alumina, nickel/tungsten, etc). Under these conditions the majority of heteroatom compounds are converted to hydrocarbons and the heteroatoms are rejected as H2S, NH3, or water. To control the exothermic heat of reaction, reactors vessels may be designed to contain several separate beds of catalyst having liquid and gas distributors or re-distributors between them. The reactor beds may be operated in a 3-phase 'trickle bed' mode whereby there are liquid and vapor reactants in contact with the solid catalyst, or in 2-phase mode where all reactants are in the vapor phase.

Products from the hydrotreating reactor are cooled in product cooler 306 to 40° C. and the pressure is reduced to 22 bar gauge (2.3 MPa) before being discharged into a high pressure separator flash drum 310. In the drum, the hydrogen-rich gas is separated from the liquid product. Hydrogen-containing off-gas from the separator is sent to the recycle gas compressor 305 which is used to circulate hydrogen back to the reactor. A slip stream containing excess hydrogen and the light gas products from the hydrotreating reactions is removed and is either re-processed to remove the contaminants in it (e.g. water, H2S, NH3, etc) or used downstream in the benzene saturation reactor. The liquid product from the high pressure separator contains some dissolved light gases that will be removed downstream in the main fractionator.

The main fractionator in the model, 320, is a packed or trayed tower that operates at about 2.6 bar gauge (0.36 MPa) pressure, contains 25 theoretical stages, an overhead condenser 321 operating at 40° C., and a bottom reboiler 322 operating at about 264° C. Feed is pre-heated in the main fractionator feed heater to 150° C. and fed to the column on about tray 18. The overhead recycle ratio is 2.5 by mass. The distillate product contains the "full-range $C_5$-$C_9$ AnelloMate product," and the bottoms product contains a $C_{10}^+$ heavy fraction. A small amount of waste gas is generated and removed from the overhead condenser accumulation drum 323.

The full-range hydrotreated AnelloMate product is suitable as feed to a conventional petroleum refinery aromatics plant, or to a separation and upgrading plant solely dedicated to processing renewable aromatics. The product is also acceptable as a gasoline blendstock.

To reduce benzene content for fuels, or to provide a benzene-rich chemicals feedstock, the full-range product can be separated further into a $C_6^-$ fraction and a $C_7^+$ fraction using a $C_6$ splitter tower. FIG. 7 shows the process flow for a $C_6$ splitter, followed by a benzene saturation unit.

The $C_6$ splitter is a trayed or packed column 400 operating at about 0.8 bar gauge (0.18 MPa), that contains 50 theoretical stages, an overhead condenser 401 operating at 40° C., and a reboiler 402 temperature of about 140° C. The reflux ratio varies between 2 and 3. A $C_6^-$ product is obtained overhead and the $C_7^+$ heavy naphtha is obtained from the bottom. The design and operation of the fractionator may be optimized to minimize the amount of toluene or heavier aromatics in the $C_6$ overhead product, and minimize the amount of benzene in the $C_7^+$ heavy naphtha product.

Minimization of toluene in the overhead product is necessary to reduce the loss of toluene by hydrogenation to methyl-cyclohexane in the benzene saturation unit, or reduce the production of methyl-ethyl- or methyl-propyl-benzenes by alkylation with ethylene or propylene, or reduce the production of methyl-long alkyl chain benzenes in linear alkyl-benzene alkylation, or reduce the amount of hydrogen consumption due to reaction with toluene, or to reduce the octane loss when toluene is converted to methyl cyclohexane by hydrogenation, or several of these reasons. Similarly, high concentrations of benzene in the $C_7$ and heavier product limit the quantity of that product that can be blended into gasoline due to strict limits on benzene content.

The $C_6^-$ stream can be used as feed stock for a benzene conversion process such as alkylation with ethylene and/or propylene to make ethylbenzene or propylbenzene, alkylated with long-chain alpha olefins to make linear alkylbenzene, or the benzene can be hydrogenated to make cyclohexane. FIG. 7 shows the benzene saturation unit. The benzene saturation reactor 410 uses high pressure hydrogen to convert benzene to cyclohexane. The flow sequence and process design is very similar to that used for hydrotreating the full-range product from the Bio-TCat™ reactor. Common catalysts for the conversion of benzene to cyclohexane include nickel on alumina or platinum on alumina. Operating pressures are 20-30 bar gauge (2.1-3.1 MPa). Temperature control is very important to avoid thermal runaway reactions due to the large exothermic heat release, and to promote the high conversion of benzene which is favored at lower temperatures. Typical temperatures around 150-205° C. are preferred. Various reactor types can be used to convert benzene to cyclohexane including trickle beds or multitubular reactors.

The cyclohexane product from the benzene saturation reactor is cooled to 40° C., and the hydrogen is flashed off at 22 bar pressure (2.3 MPa) in separator drum 420. The high pressure liquid is then sent to a flash drum 430 operating at near atmospheric pressure. Additional light gas is flashed off at these conditions. The resulting cyclohexane-rich product can be used as a solvent, as a feedstock for making nylon precursors (e.g. cyclohexanol and cyclohexanone), or used as a source of renewable gasoline blend stock.

Table 1 is a summary of the product purities obtained in the simulation. One item to note is that the recovered yields of certain products from the Bio-TCat™ process are more than what actually exited from the reactor. The increase in yields and the high recovery values are due to certain conversion processes that occurred in the hydrotreating step. For example, phenol can be converted to benzene, and cresols can be converted to toluene by hydrogenation and removal of the alcohol group from the ring. This increases the yield of desirable aromatic product. It also serves to reduce the boiling point of the mixture, for example phenol boils at 181° C. but benzene boils at 80° C. Similarly cresols boil in the 190-205° C. range, but toluene boils at 111° C.

In some embodiments a benzene-rich fraction is upgraded in a primary product upgrading process comprising the catalytic alkylation of benzene with ethylene to produce ethylbenzene or the catalytic alkylation of benzene with propylene to produce cumene and propylbenzene, or the catalytic alkylation of benzene with $C_{10}$-$C_{16}$ terminal olefins to produce LABs, or some combination of these. In practicing some embodiments of this invention, a portion of the effluent of the alkylation reaction zone is reintroduced into the alkylation reaction zone to enhance the yield of useful products via transalkylation, In embodiments that include the alkylation of benzene by ethylene or propylene, the ratio of the weight of the olefin entering the alkylation catalyst bed in the olefinic feed stream per unit time to the sum of the weights of compounds entering the alkylation catalyst bed per the same unit time, multiplied by 100, is generally less than 1.88, preferably less than 1.3, and more preferably less than 0.01. This ratio is sometimes referred to herein as the olefin ratio. When the alkylation of benzene includes reaction with $C_{10}$-$C_{16}$ olefins the weight ratio of olefin to benzene can be from 0.1 to 5, or the mole ratio of olefin to benzene can be from 0.01 to 1. The alkylation conditions may comprise a maximum olefin concentration based on the weight of compounds entering the alkylation catalyst bed of preferably less than 1.88 wt %, most preferably less than 1.3 wt %, and still more preferably less than 0.01 wt %.

The aromatic feed stream and the olefinic feed stream are preferably combined upstream of the alkylation catalyst bed. The alkylation reaction zone can comprise one or more alkylation catalyst beds and/or one or more alkylation catalyst reactors, and each reactor may contain one or more alkylation catalyst beds.

Alkylation conditions for this process include a molar ratio of phenyl groups per alkyl group of typically from 1:1 to about 25:1. In some embodiments, the molar ratio may be less than 1:1, and may be down to 0.75:1 or lower. Preferably, the molar ratio of phenyl groups per ethyl group (or propyl group, in cumene production) is below 6:1, and in some embodiments, in the range of 2:1 to 4:1.

In general, for a given molar ratio of alkylation substrate per alkylation agent, especially an olefinic alkylation agent, the greater the molar ratio of phenyl groups to alkyl groups in the feed stream, the less is the rise in temperature in the reaction zone that occurs as a result of the alkylation reactions. Although the reactor may have indirect heat exchange means to remove the heat as it is produced, the reactor is preferably adiabatic, and so the outlet temperature of the effluent stream is higher than the inlet temperature of

TABLE 1

(Composition of Bio-TCat ™ Streams)

| Volume Percent | Stream 2 Full-Range | Stream 4 C6 Minus | Stream 6 Cyclohexane | Stream 5 C7 Plus | Heavy Aromatics |
|---|---|---|---|---|---|
| Benzene | 34.4% | 94.8% | 0.0% | 0.5% | 0.0% |
| Toluene | 44.9% | 0.0% | 1.3% | 70.3% | 0.0% |
| Xylenes | 13.8% | 0.0% | 0.1% | 21.7% | 0.0% |
| EB | 0.7% | 0.0% | 0.0% | 1.2% | 0.0% |
| Styrene | 0.5% | 0.0% | 0.0% | 0.8% | 0.0% |
| C9's | 2.0% | 0.0% | 0.0% | 3.2% | 0.0% |
| C4+ Non-Aromatics | 1.5% | 3.8% | 97.7% | 0.2% | 0.3% |
| C5+ Non-Aromatics | 1.2% | 3.0% | 97.2% | 0.2% | 0.3% |
| Heavies | 1.4% | 0.0% | 0.0% | 2.2% | 100.0% |
| Light C3 Minus | 0.6% | 1.4% | 0.8% | 0.0% | 0.0% |
| Totals | 99.9% | 100.0% | 100.0% | 99.9% | 100.3% | the reactants. The appropriate reaction temperature may be preferably from 100° C. to the critical temperature of the alkylation substrate, which may be 475° C. or even higher, the inlet temperature in the reaction zone is generally from 200 to 260° C., and preferably from 230 to 250° C. The temperature rise is typically from 5 to 50° C., and preferably less than 20° C. The temperature rise in the reaction zone may be controlled by adjusting the molar ratio of phenyl groups to ethyl groups in the feed stream, for example by recycling portions of the reactor effluent. Recycling reactor effluent to the reaction zone of the alkylation reactor does not interfere in a significant way with the extent of the alkylation or transalkylation reactions, and recycling reactor effluent may be employed for the purpose of controlling reaction zone temperatures.

Alkylation is preferably performed in the liquid phase. Consequently, reaction pressure needs to be sufficiently high to ensure at least a partial liquid phase. Where ethylene is the alkylating agent olefin, the pressure range for the reactions is usually from about 200 to about 1000 psi(g) (1.4 to 7.0 MPa(g)), more commonly from about 300 to about 600 psi(g) (2.0 to 4.1 MPa(g)), and even more commonly from about 450 to about 600 psi(g) (3.1 to 4.1 MPa(g)). Preferably, the reaction conditions are sufficient to maintain benzene in a liquid phase and are supercritical conditions for ethylene. For olefins other than ethylene, this invention may be practiced generally at a pressure of from 50 to 1000 psi(g) (3.4 to 7.0 MPa(g)).

The weight hourly space velocity (WHSV) of alkylating agent ethylene preferably ranges from 0.01 to 2.0 hr$^{-1}$, whereas for $C_{10}$-$C_{16}$ olefins the WHSV is from 001 to 20 hr$^{-1}$. The WHSV of aromatics, including benzene and a polyalkylaromatic having at least two $C_2^+$ groups, if any, preferably ranges from 0.3 to 500 hr$^{-1}$.

Volatility is the property of a liquid fuel that defines its evaporation characteristics. RVP is an abbreviation for "Reid Vapor Pressure," a common measure of and generic term for gasoline volatility. RVP is a measure of the volatility of the blend, based on measurements using ASTM D-323, or subsequent ASTM methods including D-5191 and D-4814. RVP is usually expressed in units of psi because RVP is measured directly from the pressure gauge, and reported without addition of atmospheric pressure, although the units are sometimes designated as psia. RVP can be estimated by calculation by entering chemical composition data into commercially available software (e.g. Aspen™ process simulation) to calculate the RVP of the mixture. Alternatively for complex blends (e.g. "mix") where the RVP of individual streams or molecular components are known, either by measurement or by calculation, and it is desired to estimate the RVP of the resulting blend, the RVP Index method developed by Chevron Inc (Fundamentals of Petroleum Refining, by Mohamed A. Fahim, Taher A. Al-Sahhaf, Amal Elkilani, Elsevier 2010) can be used. In this method, the RVP values for each individual blend stock or molecular component is raised to the 1.25 exponent, added together using each stream's respective blending volume contribution to the pool, and then taking the 1.25 root of the sum. This is shown below in Equation (2).

$$(RVP_{mix})^{1.25} = (\Sigma(RVP_i^{1.25} * v_i))/(\Sigma v_i) \quad (2)$$

In equation (2), vi is the volume fraction of each stream making up the final gasoline blend, and $RVP_i$ is the blending RVP of each stream. $RVP_{mix}$ is the RVP of the resulting final blend.

In the U. S., the EPA has established regulations for the vapor pressure of gasoline sold at retail stations to reduce evaporative gasoline emissions that contribute to ground-level ozone and to diminish the effects of ozone-related health problems. Depending on the state and month, gasoline RVP may not exceed 9.0 psi or 7.8 psi. EPA provides a 1.0 psi RVP allowance, i.e. 1.0 psi higher RVP, for gasoline containing ethanol at 9 to 10 volume percent, meaning that gasoline blends containing this amount of ethanol may be sold at 10.0 or 8.8 psi.

In addition to the volatility requirements set forth in ASTM 4814, gasolines typically must meet a minimum octane posted at the pump, typically (R+M)/2 of 87 octane for regular grade gasoline and 91 to 93 octane for a premium grade gasoline. In many regions, refiners may offer a mid-grade gasoline having octane and additive packages placing the quality of the gasoline somewhere between regular and premium grades. A typical octane for a mid-grade gasoline is about 89.

Octane number is a measure of the knocking tendency of fuels in spark-ignited gasoline engines. Knock refers to premature thermo-chemical induced combustion ignition that occurs in the engine cylinder before the electric spark occurs. It is undesired because of potential damage to engine components. The higher the octane rating of a fuel, the less prone it is to knock in the engine. High octane fuels can also sustain higher cylinder compression which provides increased power output per engine weight (e.g. specific power) to those engines designed for high compression ratio operation.

Based on the chemical compositions, the octane number of a mixture can be estimated with reasonable accuracy using existing blending models. Octanes can be calculated using the octane number blending model of Jaffe et al (Ind. Eng. Chem. Res. 2006, 45, 337-345). Table 2 presents the octane number, the octane blending coefficient "β" (see Jaffe et al), and RVP of the compounds used in the calculations. No interaction parameters as described by Jaffe et al (e.g. $k_{12}$) were used here.

TABLE 2

(Physical Property Data for Individual Components used to calculate the Physical Properties of Products Streams)

| Compound | Density g/cm3 | RON | MON | $\beta_{RON}$ | $\beta_{MON}$ |
|---|---|---|---|---|---|
| i-pentane | 0.6244 | 92.0 | 90.3 | 2.0204 | 0.4278 |
| n-pentane | 0.6311 | 62.0 | 62.6 | 2.0559 | 0.3092 |
| hexanes & hexenes | 0.6579 | 76.0 | 73.9 | 2.0204 | 0.4278 |
| benzene | 0.8846 | 102.7 | 105.0 | 3.3984 | 0.4773 |
| cyclohexane | 0.7834 | 82.5 | 77.2 | 1.6870 | 0.2821 |
| heptanes & heptenes | 0.6881 | 90.0 | 78.0 | 2.0559 | 0.3092 |
| methyl cyclohexane | 0.7740 | 82.0 | 77.0 | 1.6870 | 0.2821 |
| toluene | 0.8717 | 118.0 | 103.5 | 3.3984 | 0.4773 |
| octanes & octenes | 0.7068 | 90.0 | 77.0 | 2.0559 | 0.3092 |
| ethyl benzene | 0.8717 | 112.0 | 105.0 | 3.3984 | 0.4773 |
| o-xylene | 0.8847 | 112.0 | 105.0 | 3.3984 | 0.4773 |
| m-xylene | 0.8689 | 112.0 | 105.0 | 3.3984 | 0.4773 |
| p-xylene | 0.8657 | 112.0 | 105.0 | 3.3984 | 0.4773 |
| nonane & nonenes | 0.7219 | 50.0 | 60.0 | 2.0559 | 0.3092 |
| C9 aromatics | 0.8664 | 110.0 | 101.0 | 3.3984 | 0.4773 |
| C10+ aromatics | 0.9650 | 105.0 | 94.0 | 3.3984 | 0.4773 |

An object of this invention is to provide valuable gasoline blendstock compositions, chemical feedstocks, or both, through the biomass upgrading processes depicted in FIGS. 1 through 7. Aromatic product fractions, produced by catalytic pyrolysis of biomass, separation of condensable materials from the raw product, mild hydrotreatment, and separation of a fraction that has a boiling point below about 185° C., and further separation of this fraction into a lighter fraction with boiling point below about 85° C., and a heavier fraction with boiling range about 85 to about 185° C. are contemplated.

One embodiment of the present invention is a renewable fuel, e.g. gasoline, processing feedstock that comprises a mixture of aromatics and paraffins produced by the steps of: a) pyrolyzing and catalytically reacting the biomass in a fluid bed reactor, b) quenching the product mixture by admixture with water or a hydrocarbon liquid, c) separating vapors from the water quench mixture, d) condensing and separating an organic phase from the vapors, e) separating the organic phase into higher boiling and lower boiling fractions, f) hydrotreating at least a portion of the lower boiling fraction, and g) recovering renewable gasoline blendstocks and chemicals therefrom. The steps of separating the organic phase into higher and lower boiling fractions and hydrotreating (steps e and f) may be reversed, i.e. step f) the hydrotreatment of the condensed materials may be conducted before or after step e) the separation into higher boiling and lower boiling fractions.

In one embodiment of the invention, step e), separation of the organic phase into higher boiling and lower boiling fractions, is conducted to separate the materials boiling about 185° C. and higher from those boiling below 185° C. After removal of the materials that boil 185° C. and higher, the mixture may comprise at least 25, or at least 35, or at least 40, or from 25 to 60, or from 35 to 55 volume % toluene, and at least 15, or at least 20, or at least 25, or from 15 to 40, or from 20 to 35 volume % benzene, and at least 5, or at least 8, or at least 10, or from 5 to 20, or from 8 to 15 volume % xylenes, and less than 15, or less than 10, or less than 5, or from 0.01 to 15, or from 2 to 10 volume % the sum of trimethylbenzenes, naphthalene, and other high boiling materials, and less than 10, or less than 5, or less than 3, or from 0.5 to 10, or from 1 to 5 volume % paraffins, and less than 0.4, or less than 0.1 weight %, or less than 100 ppm, or less than 25 ppm, or from 0.1 to 4000 ppm, or from 1 to 1000 ppm olefins by weight olefins, and less than 10, or less than 5, or less than 2 ppm, or from 0.1 to 10 ppm, or from 0.2 to 5 ppm by weight sulfur, and less than 10, or less than 5, or less than 2 ppm, or from 0.1 to 10 ppm, or from 0.2 to 5 ppm by weight nitrogen, and less than 1, or less than 0.1, or less than 0.01 weight %, or less than 100 ppm, or less than 10 ppm, or less than 1 ppm, or from 0.1 to 10000 ppm, or from 0.2 to 1000 ppm oxygen by weight. The mixture may have a calculated octane rating ((R+M)/2) of at least 100, or at least 103, or at least 105, or from 103 to 111, or from 105 to 109. The mixture may have a calculated RVP of less than 5, or less than 3, or less than 2 psi.

Other embodiments of the present invention are renewable fuel blendstocks or processing feedstocks that comprise a mixture of aromatics and paraffins produced by the steps of: pyrolyzing and catalytically reacting biomass in a fluid bed reactor, quenching the product mixture by admixture with water or a hydrocarbon liquid, separating vapors from the water quench mixture, condensing and separating an organic phase from the vapors, separating the organic phase into a higher boiling and a lower boiling fraction, hydrotreating at least a portion of the lower boiling fraction, recovering condensable products therefrom, and separating the condensed products into a fraction boiling below about 85° C. and a fraction boiling above about 85° C. The lower boiling fraction may comprise at least 75, or at least 85, or at least 90, or from 75 to 99.9, or from 85 to 99 volume % benzene by volume, and less than 20%, or less than 15%, or less than 10, or from 1 to 20, or from 5 to 10 volume % pentanes, hexanes, and heptanes by volume, and less than 20, or less than 15, or less than 10, or from 1 to 20, or from 2 to 15 volume % by volume of the sum of toluene, xylenes, ethyl benzene, and trimethylbenzenes, and less than 0.4%, or less than 0.1 weight %, or less than 100 ppm, or less than 25 ppm, or from 1 to 1000 ppm, or from 2 to 25 ppm olefins by weight, and less than 10, or less than 5, or less than 2 ppm, or from 0.01 to 10, or from 0.01 to 5 ppm by weight sulfur, and less than 10, or less than 5, or less than 2, or from 0.01 to 10, or from 0.01 to 5 ppm by weight nitrogen, and less than 1%, or less than 0.1%, or less than 0.01 weight %, or less than 100 ppm, or less than 10 ppm, or less than 1 ppm, or from 0.01 to 1000 ppm, or from 0.01 to 10 ppm oxygen by weight. The mixture may have a calculated octane rating (R+M/2) of at least 99, or at least 100, or at least 101, or from 99 to 103, or from 101 to 103. The mixture may have a calculated RVP of less than 7, or less than 5, or less than 4 psi. The higher boiling fraction may comprise at least 50%, or at least 60%, or at least 65 volume % toluene, and at least 10, or at least 15, or at least 20 volume % xylenes and less than 15, or less than 10, or less than 5 volume % benzene, and less than 15, or less than 10, or less than 6 volume % $C_9$ and higher aromatics, and less than 2, or less than 1, or less than 0.5 volume % paraffins, and less than 0.4, or less than 0.1 weight %, or less than 100 ppm, or less than 25 ppm olefins by weight, and less than 10, or less than 5, or less than 2 ppm by weight sulfur, and less than 10, or less than 5, or less than 2 ppm by weight nitrogen, and less than 1, or less than 0.1, or less than 0.01 weight %, or less than 100 ppm, or less than 10 ppm, or less than 1 ppm oxygen by weight. The mixture may have a calculated octane rating ((R+M)/2) of at least 100, or at least 105, or at least 107, or from 100 to 117, or from 105 to 111. The mixture may have a calculated RVP of less than 3, or less than 2, or less than 1.5 psi. Another embodiment of the invention comprises a mixture of the higher boiling fraction with petroleum derived materials such as gasoline wherein the higher boiling fraction comprises from 0.1 to 10 volume % and gasoline comprises from 90 to 99.9 volume % of the mixture. Another embodiment of the invention comprises a mixture of the higher boiling fraction with ethanol wherein the higher boiling fraction comprises from 1 to 25 volume % and ethanol comprises from 75 to 99 volume % of the mixture.

Another embodiment of the present invention is a renewable fuel blendstock or processing feedstock that comprises a mixture of hydrocarbons produced by the steps of: pyrolyzing and catalytically reacting biomass in a fluid bed reactor, quenching the product mixture by admixture with water or a hydrocarbon liquid, separating vapors from the water quench mixture, condensing and separating an organic phase from the vapors, separating the organic phase into higher boiling and a lower boiling fractions, hydrotreating at least a portion of the lower boiling fraction, recovering condensable products therefrom, separating the condensed products into a fraction boiling below about 85° C. and a fraction boiling about 85° C., and above, and hydrotreating the fraction boiling below about 85° C. The mixture comprises at least 80, or at least 85, or at least 90, or at least 95, or from 80 to 99 volume % cyclohexane, and less than 1%, or less than 0.1 weight %, or less than 100 ppm, or less than 10 ppm, or from 1 ppm to 1% by weight benzene, and less than 10, or less than 7, or less than 5, or from 1 to <10 volume % pentanes, hexanes, and heptanes, and less than 1, or less than 0.1 weight %, or less than 100 ppm, or less than 10 ppm, or from 1 ppm to <1 weight % by weight the sum of toluene, xylenes, trimethyl benzenes, and naphthalene, and less than 100 ppm, or less than 10 ppm, or less than 1 ppm, or from 0.1 to <100 ppm olefins by weight, and less than 5, or less than 2, or less than 1 ppm, or from 0.1 to <5 ppm by weight sulfur, and less than 10, or less than 5, or less than 2 ppm, or from 1 to <10 ppm by weight nitrogen, and less than 1%, or less than 0.1%, or less than 0.01 weight %, or less than 100 ppm, or less than 10 ppm, or less than 1 ppm, or from 1 ppm to <0.1 weight % oxygen. The mixture may have a calculated octane rating ((R+M)/2) of at least 70, or at least 75, or at least 80, or from 75 to 80, or from 76 to 77. The mixture may have a calculated RVP of less than 7, or less than 5, or less than 4, or from 2 to <7, or from 3 to 5 psi. Another embodiment of the invention comprises a mixture of the hydrotreated lower boiling fraction with petroleum derived materials. The mixture may be further purified to provide a high purity chemical feedstock quality cyclohexane that comprises at least 95, or at least 99, or at least 99.5% cyclohexane. Another embodiment of the invention comprises a mixture of the hydrotreated fraction with petroleum derived materials such as gasoline wherein the hydrotreated fraction comprises from 0.1 to 10 volume % and gasoline comprises from 90 to 99.9 volume % of the mixture. Another embodiment of the invention comprises a mixture of the hydrotreated fraction with ethanol wherein the hydrotreated fraction comprises from 1 to 25 volume % and ethanol comprises from 75 to 99 volume % of the mixture %, or at least 99%, or at least 99.5% cyclohexane.

The hydrotreatment of the lower boiling fraction may be conducted by contacting the liquid with a $H_2$ containing gas at a pressure from 0.1 MPa to 10 MPa (1 to 100 atm), preferably 0.2 to 2 MPa (2 to 20 atm) at a temperature from 40 to 350° C., preferably from 40 to 200° C., in the presence of a solid catalyst. Solid catalysts useful for the hydrotreating process include Ni, Co, Fe, Cu, Zn, Ag, Pt, Pd, Ru, Rh, Ir, Mo, W, or combinations thereof, deposited on oxide supports including oxides of Al, Si, Ti, Zr, Th, Mg, Ca, or some combination of these, either as crystalline solids or as amorphous mixtures. In some cases the catalyst may comprise chlorinated alumina, a zeolitic alumina, active carbon, clays, aluminous cements, rare earth oxides, or alkaline-earth oxides. The hydrotreatment can be carried out in a fixed bed, trickle bed, catalytic distillation reactor, multi-tubular reactor, or fluid bed reactor, with counter- or co-current flow of feed and hydrogen. Suitable conditions and operation of distillation reactors are described in U.S. Pat. No. 8,808,533, and United States Patent Publication 2010/0063334, incorporated herein by reference.

Another embodiment of the present invention is a renewable fuel blendstock that comprises a mixture of aromatics and paraffins produced by the steps of pyrolyzing and catalytically reacting biomass in a fluid bed reactor, quenching the product mixture by admixture with water or a hydrocarbon liquid, separating vapors from the water quench mixture, condensing and separating an organic phase from the vapors, separating the organic phase into a higher boiling and a lower boiling fraction, hydrotreating at least a portion of the lower boiling fraction, recovering condensable products therefrom, separating the condensed products into a fraction boiling below about 85° C. and a fraction boiling above about 85° C., hydrotreating the fraction boiling below about 85° C., and combining the separated higher boiling fraction and the hydrotreated fraction boiling below about 85° C. The mixture may comprise from 1 to 99 volume % of the hydrotreated materials boiling below 85° C., and from 1 to 99% by volume of the material boiling at or above 85° C. The mixture comprises at least 10, or at least 20, or at least 25, or at least 27, or from 10 to 40 volume % cyclohexane, and at least 30, or at least 35, or at least 40, or at least 45, or from 30 to 60 volume % toluene, and at least 5, or at least 10, or at least 14, or from 5 to 25 volume % xylenes, and less than 10, or less than 5, or less than 3, or from 1 to <10 volume % benzene, and less than 5, or less than 3, or less than 2, or from 0.1 to <5 volume % hexanes and pentanes, and less than 1, or less than 7, or less than 5, or from 1 to <10 volume % the sum of trimethylbenzenes and naphthalene, and less than 0.4, or less than 0.1 weight %, or less than 100 ppm, or less than 25 ppm, or less than 1 ppm, or from 0.1 ppm to <0.4 weight % olefins, and less than 5, or less than 2, or less than 1 ppm, or from 0.1 to <5 ppm by weight sulfur, and less than 10, or less than 5, or less than 2 ppm, or from 0.1 to <10 ppm by weight nitrogen, and less than 1, or less than 0.1, or less than 0.01 weight %, or less than 100 ppm, or less than 10 ppm, or less than 1 ppm, or from 0.1 ppm to <1 weight %, or from 0.1 to 100 ppm oxygen by weight. The mixture may have a calculated octane rating ((R+M)/2) of at least 95, or at least 97, or at least 100, or from 95 to 110, or from 97 to 105. The mixture may have a calculated RVP of less than 5, or less than 3, or less than 2, or from 0.1 to <5 psi. Another embodiment of the invention comprises the mixture of the above mixture with petroleum derived materials, or ethanol, or both in a gasoline product. Another embodiment of the invention comprises a mixture of this renewable mixture with petroleum derived materials such as gasoline wherein the renewable mixture comprises from 0.1 to 10 volume % and gasoline comprises from 90 to 99.9 volume % of the mixture. Another embodiment of the invention comprises a mixture of the renewable mixture with ethanol wherein the renewable mixture comprises from 1 to 25 volume % and ethanol comprises from 75 to 99 volume % of the mixture.

Gasoline is a complex mixture of many hundreds of individual chemicals, made from various blend stocks that are produced in a refinery or produced elsewhere and blended either at the refinery or at the distribution terminal (e.g. ethanol splash blending). To meet technical, regulatory, and commercial requirements, the gasoline finished blend must meet several constraints including limits on vapor pressure, benzene content, sulfur, octane, etc., and minimum volumes to sell into the consumer market while realizing a profit. Therefore it is possible that more than one combination and proportion of various blend stocks can result in a finished gasoline meeting all of the constraints and requirements. Due to both the importance of and difficulty in identifying profitable blends meeting specifications, refiners generally rely on advanced computational tools, primarily Linear or Non-Linear Programming methods ("LPs"), to accomplish their goals.

In one embodiment, a gasoline blending system can be used to combine a petroleum-derived gasoline with at least a portion of the renewable biomass derived blendstocks of the inventive process to produce renewable gasoline compositions. The renewable gasoline composition can comprise petroleum-derived gasoline in an amount of at least 80, or 85, or 90, or 95 volume %, and/or up to 96, or 98, or 99, or 99.5, volume %; or from 80 to 99.5, or from 90 to 98 volume %, and the renewable blendstock fraction in an amount of at least 0.1, or 0.5, or 1, or 5, volume % and/or up to 20, or 15, or 10, or 5, volume %, or from 0.1 to 20, or from 1 to 10 volume %. The renewable gasoline compositions may have octane ratings ((R+M)/2) of at least 87, or at least 90, or at least 92, RVP of less than 10, or less than 9, or less than 8, or from 5 to 10 psi, sulfur contents of less than 30, or less than 20, or less than 10, or from 1 to 30, or from 2 to 20 ppm, aromatics contents of less than 30, or less than 25 or less than 16 volume %, or at least 5, or at least 10, or at least 15, or from 5 to 30, or from 15 to 25 volume %.

Alternatively, in another embodiment, a gasoline blending system can be used to combine a petroleum derived gasoline with ethanol and at least a portion of the renewable biomass derived blendstocks of the inventive process to produce renewable gasoline compositions. The renewable gasoline composition can comprise petroleum-derived gasoline in an amount of at least 80, or 85, or 90, or 95 volume percent and/or at most 96, or 98, or 99, or 99.5, volume percent; or from 80 to 99.5, or from 90 to 98 volume %, ethanol in an amount of at least 1, or at least 5, or at least 10, or up to 25, or up to 20, or up to 15 or up to 10 volume percent, or from 1 to 20, or from 5 to 15 volume %, and the renewable blendstock fraction in an amount of at least 0.1, or 0.5, or 1, or 5, or 8, volume % or up to 20, or 15, or 10, or 5, or from 0.1 to 20, or from 1 to 10 volume %. The renewable gasoline compositions may have octane ratings ((R+M)/2) of at least 87, or at least 90, or at least 92, RVP of less than 10, or less than 9, or less than 8, or from 5 to <10 psi, sulfur contents of less than 30, or less than 20, or less than 10, or from 1 to <30, or from 2 to 20 ppm, aromatics contents of less than 30, or less than 25 or less than 16 volume percent, or at least 5, or at least 10, or at least 15, or from 5 to 30, or from 15 to 25 volume %.

Alternatively, in another embodiment, a gasoline blending system can be used to combine ethanol and at least a portion of the renewable biomass derived blendstocks of the inventive process to produce essentially 100% renewable gasoline compositions. The renewable gasoline composition can comprise ethanol in an amount of at least 60, or 70, or 80, or 85, volume percent and/or up to 90, or 95, or 99, volume percent; or from 70 to 99, or from 80 to 90 volume %, and the renewable blendstock fraction in an amount of at least 1, or at least 5, or at least 10, or at least 15, or up to 40, or up to 30, or up to 20, or up to 15 volume %, or from 1 to 40, or from 5 to 15 volume %. The renewable gasoline compositions may have octane ratings ((R+M)/2) of at least 87, or at least 90, or at least 92, or at least 100, RVP of less than 10, or less than 9, or less than 8, or less than 6, or from 3 to 9 psi, sulfur contents of less than 30, or less than 20, or less than 15, or from 1 to <30, or from 2 to 20 ppm, aromatics contents of less than 30, or less than 25 or less than 16 volume %, or at least 5, or at least 10, or at least 15, or from 5 to <30, or from 10 to 25 volume %.

The following Examples demonstrate the present invention and its capability for use. The invention is capable of other and different embodiments, and its several details are capable of modifications in various apparent respects, without departing from the spirit and scope of the invention. Accordingly, the Examples are to be regarded as illustrative in nature and not as restrictive. All percentages are by weight unless otherwise indicated.

Example 1

An Aspen™ model was prepared to evaluate the Bio-TCat™ process and product upgrading and separation processes in FIGS. 1, 2, 3, and 4. In the model a mixture of materials simulating the raw liquid product condensed from the Bio-TCat™ process was hydrotreated under mild conditions to produce a product stream that has reduced concentrations of sulfur, nitrogen, olefins, dienes, oxygenates, and other impurities. The whole hydrotreated stream may be identified as the "$C_5^+$ Liquid Product" and a fraction from which the higher boiling materials have been separated by distillation may be identified as a "$C_5$-$C_9$ Product Cut," identified as stream 1 in FIGS. 1, 2, 3, and 4. The $C_5^+$ Liquid Product comprises all molecules with carbon numbers of 5 or more, including molecules that boil outside of the gasoline range. The $C_5$-$C_9$ Product Cut boils in the gasoline range and is a partially refined product contained within the $C_5^+$ product. It is obtained by distillation of the $C_5^+$ product. After mild hydrotreating, model calculations show that the concentration of heteroatom species in the $C_5$-$C_9$ Product Cut is less than 1 ppm of sulfur, less than 1 ppm of nitrogen, and olefins, dienes, and styrenes contents are also reduced to less than 100 ppm. The $C_5$-$C_9$ Bio-TCat™ product after mild hydrotreating is called "AnelloMate Full Range Product". The compositions of the various fractions were calculated using the model and are collected in Table 3 (all values are ppm by weight).

TABLE 3

(Composition of Bio-TCat ™ Product ($C_5^+$ Liquid Product) and AnelloMate Full Range ($C_5$-$C_9$ Product Cut) products before and after Mild Hydrotreating (HDT)

| Heteroatoms & Unsaturates ppmw | Composition of Liquid Product Before HDT | | Composition of Liquid Product After HDT | |
|---|---|---|---|---|
| | C5+ Liquid Product | C5-C9 Product Cut | C5+ Liquid Product | C5-C9 Product Cut |
| Oxygen | 7,959 | 3,479 | <1 | <1 |
| Sulfur | 59 | 74 | <1 | <1 |
| Nitrogen | 335 | 434 | <1 | <1 |
| C5+ Olefins | 5,958 | 8,994 | <100 | <100 |
| C5+ Dienes | 0 | 0 | <100 | <100 |
| Styrenes | 4,727 | 6,134 | <100 | <100 |

The results in Table 3 show that mild hydrotreating of the whole liquid product of the Bio-TCat™ process and the $C_5$-$C_9$ product cut separated therefrom results in a product stream that has sulfur, nitrogen, and oxygen concentrations that are below detection limits, i.e. less than 1 ppm, and that the concentration of olefins and dienes is below 100 ppm indicating that the stream is a valuable feed for gasoline blendstocks or chemicals production.

Example 2

A computational model of the inventive process as depicted in FIG. 1 was developed in Aspen™. The Benfree™ benzene hydrogenation process conversions and selectivities were obtained from commercial sources. In Table 4 are collected the compositions of the various product streams as calculated in the computational model. The lower section of Table 4 includes the fuel-relevant physical properties of the various streams including density, the volume percent of each stream relative to the starting Bio-TCat™ full-range product, and calculated octane numbers and vapor pressures.

The volume percentages after separation, hydrogenation, and recombination add up to a number above 100%. This phenomenon is well-known in the oil refining industry where it is referred to as "volume swell". While mass is conserved in any system, volume is not necessarily conserved. Volume swell occurs because of density changes that occur when molecules are converted from one type to another. In this case, the volume swell is attributed to conversion of benzene to cyclohexane, where the densities of the pure compounds are 885 and 785 kg/m³, respectively (reference NIST Standard Reference Database 69: NIST Chemistry WebBook).

Based on the chemical compositions, the octane numbers of the mixtures obtained from the process model have been estimated using the chemical compositions in Table 3 with the octane number blending model of Jaffe et al (Ind. Eng. Chem. Res. 2006, 45, 337-345).

Based on the chemical compositions obtained from the process model the Reid Vapor Pressures of the product mixtures are presented in Table 4. The calculation was performed using Equation 2, above, wherein vi is the volume fraction of each stream making up the final gasoline blend, $RVP_i$ is the blending RVP of each stream, and RVPmix is the RVP of the resulting final blend. The calculated RVP of each AnelloMate stream based on the RVP of each identifiable chemical compound is presented in Table 4 (percentages in volume).

using literature sources for refinery stream yields and blending properties. This model was then used to create finished gasoline blends containing targeted percentages of renewable content using ethanol and AnelloMate products, either alone or as combinations of each, blended into a gasoline base blend ("BOB" or blendstock for oxygenate blending"). In the LP model, the refinery is assumed to have a source of n-butane for RVP control, a naphtha hydrotreater to reduce sulfur, a $C_5/C_6$ paraffin isomerization unit, a light naphtha benzene saturation unit, a fluid catalytic cracker (FCC), a FCC naphtha post-hydrotreater unit, a sulfuric acid alkylation unit, and a naphtha reformer. Operation of these units is constrained by throughput and mass balance. The current target of the EPA is that renewables should contribute at least 10 volume percent to the pool. For ethanol, there is also a

TABLE 4

(Compositions and Properties of Product Streams of the Process in FIG. 1)

| | Streams | | | | |
|---|---|---|---|---|---|
| Compound, vol % | 1 AnelloMate Full-Range Product | 4 AnelloMate C6-Splitter Light Naphtha | 6 AnelloMate Light Naphtha After Benzene Saturation | 5 AnelloMate C7-C9 Heavy Naphtha from C6-Splitter | 5 + 6 AnelloMate Combined Cyclohexane + C7-C9 |
| i-pentane | 0.1% | 0.2% | 0.1% | 0.0% | 0.0% |
| n-pentane | 0.3% | 0.8% | 0.5% | 0.0% | 0.2% |
| hexanes & hexenes | 0.6% | 1.7% | 1.4% | 0.0% | 0.5% |
| benzene | 34.9% | 97.0% | 0.0% | 1.9% | 1.2% |
| cyclohexane | 0.0% | 0.0% | 97.8% | 0.0% | 36.3% |
| heptanes & heptenes | 0.2% | 0.3% | 0.3% | 0.2% | 0.2% |
| methyl cyclohexane | 0.0% | 0.0% | 0.0% | 0.0% | 0.0% |
| toluene | 45.5% | 0.0% | 0.0% | 69.6% | 43.8% |
| octanes & octenes | 0.2% | 0.0% | 0.0% | 0.2% | 0.1% |
| ethyl benzene | 0.8% | 0.0% | 0.0% | 1.2% | 0.7% |
| o-xylene | 2.9% | 0.0% | 0.0% | 4.4% | 2.8% |
| m-xylene | 6.7% | 0.0% | 0.0% | 10.3% | 6.5% |
| p-xylene | 4.4% | 0.0% | 0.0% | 6.7% | 4.2% |
| nonane & nonenes | 0.1% | 0.0% | 0.0% | 0.1% | 0.1% |
| C9 aromatics | 2.1% | 0.0% | 0.0% | 3.2% | 2.0% |
| C10+ aromatics | 1.4% | 0.0% | 0.0% | 2.2% | 1.4% |
| Total | 100.0% | 100.0% | 100.0% | 100.0% | 100.0% |
| Density @ 15 C/4, kg/m3 | 873 | 878 | 781 | 871 | 837 |
| Calculated RON | 111 | 102 | 82 | 116 | 108 |
| Calculated MON | 104 | 104 | 77 | 103 | 97 |
| Calculated (R + M/2) | 107 | 103 | 80 | 110 | 102 |
| Calculated RVP, psia | 1.9 | 3.2 | 3.1 | 1.0 | 1.9 |
| Total Aromatics | 98.6% | 97.0% | 0.0% | 99.5% | 62.6% |

The data in Table 4 show that valuable gasoline blending stocks can be prepared from the products of the Bio TCat™ process according to the scheme depicted in FIG. 1. The data in Table 4 show that blendstocks prepared by the inventive process including pyrolyzing and catalytically reacting the biomass in a fluid bed reactor, quenching the product mixture by admixture with water or a hydrocarbon liquid, separating vapors from the water quench mixture, condensing and separating an organic phase from the vapors, hydrotreating at least a portion of the condensed organic phase have physical properties that can be useful for blending with gasoline to provide fuel mixtures that meet regulatory standards with respect to octane, benzene content, sulfur content, or RVP.

Example 3

A gasoline blending Linear Programming model was written in Excel-Solver to describe a generic refinery operation and the various blend stocks that are produced within it regulated minimum level of 5.9 volume percent in some states. This represents a further constraint on blending calculations.

The LP model was run to make variable amounts of a finished gasoline having properties that meet regulatory, technical, and commercial requirements. Specific specification limits included;

Benzene content less than 0.62 volume % (U.S. pool average requirement)
Sulfur content less than 10 ppm (U.S. 2017 requirement)
RVP of less than 7.8 (Summer season requirement)
Total aromatics less than 25 volume % (CARB gasoline requirement)
87 (R+M)/2 octane (regular grade gasoline)

Table 5 shows the properties of the renewable fuel component used in the Linear Programming model to make the finished gasoline. Table 6 shows several blend compositions and blend properties calculated with the Linear Programming model for various BOB/Ethanol/AnelloMate mixtures. For ethanol-only blending, the 1 psi waiver allowance was not used.

TABLE 5

(Gasoline blending properties for AnelloMate products, ethanol, and gasoline specifications)

| | Refinery Gasoline BOB | AnelloMate Full-Range C5-C9 | AnelloMate Hydro-Treated C6 | AnelloMate C7-C9 Heavy Naphtha | Splash Blended Ethanol |
|---|---|---|---|---|---|
| Renewable Content, vol % | 0% | 100% | 100% | 100% | 100% |
| Benzene, vol % | 0.41% | 34.86% | 0.00% | 1.92% | 0.00% |
| Sulfur, ppm | 7.0 | 0.5 | 0.0 | 0.5 | 20 |
| RVP, psi | 6.0 | 0.8 | 1.5 | 0.4 | 33.9 |
| RVP Index | 9.4 | 0.8 | 1.7 | 0.3 | 81.7 |
| Total Olefins, vol % | 13.4% | 0.0% | 0.0% | 0.0% | 0.0% |
| Total Aromatics, vol % | 24.3% | 98.6% | 0.0% | 99.5% | 0.0% |
| Octane (R + M)/2 | 85.4 | 107.4 | 79.7 | 109.6 | 113 |

TABLE 6

(Fuel Blend Compositions and Properties for Ethanol and AnelloMate with Gasoline)

| Blended Fuel | Target Specification | 10% Ethanol | 87 Octane Gasoline with AnelloMate and Ethanol | 90 Octane Gasoline with AnelloMate and Ethanol | 100% Renewable Gasoline with 85% Ethanol and 15% AnelloMate |
|---|---|---|---|---|---|
| Blend Stocks, Volume % | | | | | |
| Refinery Gasoline, BOB | — | 90% | 90% | 76.2% | 0.0% |
| AnelloMate Hydrotreated C6 | — | — | 1.3% | 2.7% | 4.6% |
| AnelloMate C7-C9 Heavy Naphtha | — | — | 2.8% | 6.1% | 10.4% |
| Splash Blended Ethanol | — | 10% | 5.9% | 15.0% | 85.0% |
| Blend Parameters | | | | | |
| Renewable Content, vol % | 10.0% | 10.0% | 10.0% | 23.8% | 100.0% |
| Benzene Maximum, vol % | 0.62% | 0.37% | 0.42% | 0.43% | 0.20% |
| Sulfur Maximum, ppm | 10 | 8.3 | 7.5 | 8.4 | 17.1 |
| RVP Maximum, psi | 7.8 | 7.8 | 7.8 | 8.5 | 5.6 |
| Total Olefins, vol % | — | 12.1% | 12.1% | 10.2% | 0.0% |
| Total Aromatics Maximum, vol % | 25% | 21.8% | 24.7% | 23.0% | 10.4% |
| Octane Minimum (R + M)/2 | 87 | 87.5 | 87.6 | 90.3 | 110.7 |
| Energy Content Versus Gasoline, % | — | 96.8% | 98.1% | 95.2% | 72.8% |

The results in Table 6 show that gasoline blendstocks prepared by the steps of pyrolyzing and catalytically reacting the biomass in a fluid bed reactor, quenching the product mixture by admixture with water or a hydrocarbon liquid, separating vapors from the water quench mixture, condensing and separating an organic phase from the vapors, and hydrotreating at least a portion of the condensed products, can be useful for blending with gasoline to provide fuel mixtures that meet regulatory standards and in some cases have higher octane, lower benzene, lower sulfur, lower RVP, or lower RVP Index, or some combination of these features compared to 10% ethanol in gasoline fuel.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A catalytic fast pyrolysis process for preparing chemicals comprising steps of:
    i) feeding biomass, catalyst composition, and transport fluid to a catalytic fast pyrolysis process fluidized bed reactor maintained at reaction conditions to manufacture a raw fluid product stream,
    ii) feeding the raw fluid product stream of step i) to a solids separation and stripping system to produce separated solids and a fluid product stream,
    iii) feeding the fluid product stream of step ii) to a quench vapor/liquid separation system utilizing water or hydrocarbon quench to produce a liquid phase stream comprising water, char, coke, ash, catalyst fines, oxygenates, and $C_9^+$ aromatics, and a vapor phase stream comprising carbon monoxide, carbon dioxide, hydrogen, olefins, and aromatics, said aromatics selected from the group consisting of benzene, toluene, xylenes, phenols, naphthols, benzofuran, ethylbenzene, styrene, naphthalene, methylnaphthalene and combinations thereof, iv) feeding the vapor phase stream of step iii) to a condensation system to produce an organic phase stream, v) feeding the organic phase stream of step iv) to a separation system to produce a high boiling fraction and a low boiling fraction, vi) feeding the low boiling fraction of step v) to a separation system to produce a fraction boiling above 85° C. and a fraction boiling below 85° C., vii) hydrogenating at least a portion of the fraction boiling below 85° C. of step vi) at hydrogenating conditions to produce a hydrogenated fraction, and viii) recovering chemicals comprising at least 10% by volume cyclohexane from the hydrogenated fraction of step vii), in a product recovery system.

2. The process of claim 1 wherein the catalyst composition of step i) comprises a crystalline molecular sieve characterized by a silica/alumina mole ratio greater than 12 and a Constraint Index from 1 to 12.

3. The process of claim 1 wherein the biomass of step i) comprises solids.

4. The process of claim 1 wherein the reaction conditions of step i) include a temperature of from 300 to 1000° C. and pressure from 0.1 to 1.5 MPa; and the hydrotreating conditions of step vii) include contacting the fraction boiling below 85° C. with a hydrogen-containing stream at a temperature of from 40 to 350° C. and pressure from 0.1 to 40 MPa.

5. The process of claim 1 wherein the catalyst composition of step i) comprises a crystalline molecular sieve having the structure of ZSM-5, ZSM-11, ZSM-12, ZSM-22, ZSM-23, ZSM-35, ZSM-48, ZSM-50 or combinations thereof.

6. A catalytic fast pyrolysis process for preparing chemicals comprising steps of:
i) feeding biomass, catalyst composition, and transport fluid to a catalytic fast pyrolysis process fluidized bed reactor maintained at reaction conditions to manufacture a raw fluid product stream,
ii) feeding the raw fluid product stream of step i) to a solids separation and stripping system to produce separated solids and a fluid product stream,
iii) feeding the fluid product stream of step ii) to a quench vapor/liquid separation system utilizing water or hydrocarbon quench to produce a liquid phase stream comprising water, char, coke, ash, catalyst fines, oxygenates, and $C_9^+$ aromatics, and a vapor phase stream comprising carbon monoxide, carbon dioxide, hydrogen, olefins, and aromatics, said aromatics selected from the group consisting of benzene, toluene, xylenes, phenols, naphthols, benzofuran, ethylbenzene, styrene, naphthalene, methylnaphthalene and combinations thereof,
iv) feeding the vapor phase stream of step iii) to a condensation system to produce an organic phase stream,
v) feeding the organic phase stream of step iv) to a separation system to produce a high boiling fraction and a low boiling fraction,
vi) feeding the low boiling fraction of step v) to a separation system to produce a fraction boiling above 78° C. and a fraction boiling below 78° C.,
vii) hydrogenating at least a portion of the fraction boiling below 78° C. of step
vi) at hydrogenating conditions to produce a hydrogenated fraction, and
viii) recovering chemicals comprising at least 10% cyclohexane from the hydrogenated fraction of step vii), in a product recovery system.

7. A catalytic fast pyrolysis process for preparing chemicals comprising steps of:
i) feeding biomass, catalyst composition, and transport fluid to a catalytic fast pyrolysis process fluidized bed reactor maintained at reaction conditions to manufacture a raw fluid product stream,
ii) feeding the raw fluid product stream of step i) to a solids separation and stripping system to produce separated solids and a fluid product stream,
iii) feeding the fluid product stream of step ii) to a quench vapor/liquid separation system utilizing water or hydrocarbon quench to produce a liquid phase stream comprising water, char, coke, ash, catalyst fines, oxygenates, and $C_9^+$ aromatics, and a vapor phase stream comprising carbon monoxide, carbon dioxide, hydrogen, olefins, and aromatics, said aromatics selected from the group consisting of benzene, toluene, xylenes, phenols, naphthols, benzofuran, ethylbenzene, styrene, naphthalene, methylnaphthalene and combinations thereof,
iv) feeding the vapor phase stream of step iii) to a condensation system to produce an organic phase stream,
v) hydrotreating the organic phase stream of step iv) at hydrotreating conditions to produce a hydrotreated stream,
vi) feeding the hydrotreated stream of step v) to a separation system to
produce a high boiling fraction and a low boiling fraction,
vii) feeding the low boiling fraction of step vi) to a separation system to produce a fraction boiling above 78° C. and a fraction boiling below 78° C.,
viii) hydrogenating at least a portion of the fraction boiling below 78° C. of step
vii) at hydrogenating conditions to produce a hydrogenated fraction, and
ix) recovering chemicals comprising at least 10% cyclohexane from the hydrogenated fraction of step viii), in a product recovery system.

8. The process of claim 7 wherein the high boiling fraction of step vi) contains less than 10 ppm by weight sulfur, or the low boiling fraction of step vi) contains less than 10 ppm by weight sulfur, or both.

9. The process of claim 1 wherein the organic phase stream fed to step v) contains less than 10 ppm by weight sulfur.

10. The process of claim 6 wherein step viii) comprises recovering a blendstock comprising at least 30 volume % toluene, less than 10 volume % benzene, at least 5 volume % xylenes, less than 5 volume % total pentanes and hexanes, less than 10 volume % total trimethylbenzenes and naphthalene, and at least 10 volume % cyclohexane, said blendstock having a calculated octane rating ((R+M)/2) of at least 95, and a calculated Reid Vapor Pressure (RVP) of less than 5 psia.

11. The process of claim 7 wherein step ix) comprises recovering a mixture comprising at least 10 volume % cyclohexane, at least 30 volume % toluene, and at least 5 volume % xylenes, less than 10 volume % benzene, and less than 5 volume % hexanes and pentanes, and less than 1 volume % the sum of trimethylbenzenes and naphthalene, and less than 0.4 weight % olefins, and less than 5 ppm by weight sulfur, and less than 10 ppm by weight nitrogen, and less than 1 weight % oxygen.

12. The process of claim 1 wherein the high boiling fraction of step v) is at a temperature of 185° C.

13. The process of claim 6 wherein the catalyst composition of step i) comprises a crystalline molecular sieve characterized by a silica/alumina mole ratio greater than 12 and a Constraint Index from 1 to 12.

14. The process of claim 6 wherein the biomass of step i) comprises solids.

15. The process of claim 6 wherein the reaction conditions of step i) include a temperature of from 300 to 1000° C. and pressure from 0.1 to 1.5 MPa; and the hydrotreating conditions of step vii) include contacting the fraction boiling below 78° C. with a hydrogen-containing stream at a temperature of from 40 to 350° C. and pressure from 0.1 to 40 MPa.

16. The process of claim 6 wherein the catalyst composition of step i) comprises a crystalline molecular sieve having the structure of ZSM-5, ZSM-11, ZSM-12, ZSM-22, ZSM-23, ZSM-35, ZSM-48, ZSM-50 or combinations thereof.

17. The process of claim 6 wherein the organic phase stream fed to step v) contains less than 10 ppm by weight sulfur.

* * * * *